United States Patent
Jäger et al.

(10) Patent No.: US 12,390,470 B2
(45) Date of Patent: Aug. 19, 2025

(54) 1-METHYLXANTHINE-BASED BIOACTIVE COMPOSITION AND METHOD OF USE THEREOF

(71) Applicant: Ingenious Ingredients, LP, Lewisville, TX (US)

(72) Inventors: Ralf Jäger, Whitefish Bay, WI (US); Martin Purpura, Spring, TX (US); Shawn Wells, Frisco, TX (US); Kylin Liao, Plano, TX (US)

(73) Assignee: Ingenious Ingredients, LP, Lewisville, TX (US)

( * ) Notice: Subject to any disclaimer, the term of this patent is extended or adjusted under 35 U.S.C. 154(b) by 0 days.

(21) Appl. No.: 17/715,911

(22) Filed: Apr. 7, 2022

(65) Prior Publication Data

US 2022/0331328 A1    Oct. 20, 2022

Related U.S. Application Data

(60) Provisional application No. 63/171,943, filed on Apr. 7, 2021, provisional application No. 63/171,925, filed on Apr. 7, 2021, provisional application No. 63/172,007, filed on Apr. 7, 2021, provisional application No. 63/208,856, filed on Jun. 9, 2021.

(51) Int. Cl.
*A61K 31/522* (2006.01)
*A61K 45/06* (2006.01)

(52) U.S. Cl.
CPC ............ *A61K 31/522* (2013.01); *A61K 45/06* (2013.01)

(58) Field of Classification Search
CPC ............................... A61K 31/522; A61K 45/06
See application file for complete search history.

(56) References Cited

U.S. PATENT DOCUMENTS

| | | |
|---|---|---|
| 2007/0224292 A1 | 9/2007 | Brunner et al. |
| 2015/0196579 A1 | 7/2015 | Ferrante et al. |
| 2016/0339078 A1 | 11/2016 | Hamill |
| 2018/0235970 A1 | 8/2018 | Zemel et al. |
| 2019/0038640 A1 | 2/2019 | Notelovitz |
| 2020/0077689 A1 | 3/2020 | Lee |
| 2021/0068429 A1 | 3/2021 | Sippy |
| 2021/0121469 A1 | 4/2021 | Bhargava |
| 2022/0331327 A1 | 10/2022 | Jager et al. |

FOREIGN PATENT DOCUMENTS

| | | | |
|---|---|---|---|
| JP | 2799178 B2 | 9/1998 | |
| WO | WO-2006024545 A1 * | 3/2006 | ............ A61K 31/12 |
| WO | 2011113066 A1 | 9/2011 | |
| WO | 2013120481 A2 | 8/2013 | |
| WO | 2013173265 A1 | 11/2013 | |
| WO | 2021151094 A1 | 7/2021 | |
| WO | 2023009681 A1 | 2/2023 | |

OTHER PUBLICATIONS

Wikipedia, "Caffeine", Wikipedia, Dec. 31, 2020.
Lee, Chul, "Antioxidant ability of caffeine and its metabolites based on the study of oxygen radial absorbing capacity and inhibition of LDL peroxidation", Clinica Chimca Acta, Jan. 18, 2000, pp. 141-154, vol. 295.
Ferree, et al., "Paraxanthine: Connecting Caffeine to Nitric Oxide Neurotransmission", Journal of Caffeine Research, No. 3, Nov. 2, 2013, 1-7.
Dammann, Kristen W., et al., "Effects of consumption of sucromalt, a slowly digestable carbohydrate, on mental and physical energy questionnaire responses", Nutritional Neuroscience, vol. 16, No. 2, 2013, 83-95.
Decker, Kimberly, "Leveling Up: Esports enthusiasts target deitary supplements to up their game", Nutritional Outlook, Apr. 1, 2020, 66-70.
Mtale, Kenneth, et al., "Nutrition and Supplement Update for the Endurance Athlete: Review and Recommendations", Nutrients, Jun. 11, 2019.
Anonymous, "Urine Therapy", Wikipedia; URL:https://en.wikipedia.org/wiki/Urine_therapy, Nov. 6, 2024.
Monteiro, Joao, et al., "Pharmacological potential of methylxanthines: Retrospective analysis and future expectations", Critical Reviews in Food Science and Nutrition; vol. 59, No. 16, May 15, 2018, 2597-2625.
Suzuki, Takeo, et al., "Biosynthesis of Caffeine by Tea-Leaf Extracts", Biochemical Journal, vol. 146, Portland Press, Jan. 1, 1975, 87-96.

\* cited by examiner

*Primary Examiner* — San Ming R Hui
(74) *Attorney, Agent, or Firm* — Dentons Davis Brown, P.C.; Matthew Coryell

(57) ABSTRACT

The disclosed compositions, systems and methods relate to a dietary supplement for human consumption and comprises 1-methylxanthine and optionally other compounds that modulate the effects of 1-methylxanthine. Uses for the 1-methylxanthine-containing supplements contain improvement of at least one of endurance performance, mood, vigor, lipolysis, energy expenditure, exercise performance, and/or decreased appetite.

13 Claims, No Drawings

1-METHYLXANTHINE-BASED BIOACTIVE COMPOSITION AND METHOD OF USE THEREOF

CROSS-REFERENCE TO RELATED APPLICATION(S)

This application claims priority to U.S. Provisional Application No. 63/171,943, filed Apr. 7, 2021 and entitled "1-METHYLXANTHINE-BASED BIOACTIVE COMPOSITION AND METHOD OF USE THEREOF," U.S. Provisional Application No. 63/171,925 filed Apr. 7, 2021 and entitled "7-METHYLXANTHINE-BASED BIOACTIVE COMPOSITION AND METHOD OF USE THEREOF," U.S. Provisional Application No. 63/172,007 filed Apr. 7, 2021, and entitled "COMBINATION OF 1-METHYLXANTHINE AND 7-METHYLXANTHINE-BASED BIOACTIVE COMPOSITION AND METHOD OF USE THEREOF," and U.S. Provisional Application No. 63/208,856 filed Jun. 9, 2021 and entitled "COMBINATION OF PARAXANTHINE AND 1-METHYLXANTHINE-BASED BIOACTIVE COMPOSITION AND METHOD OF USE," each of which is hereby incorporated by reference in its entirety under 35 U.S.C. § 119(e).

TECHNICAL FIELD

The disclosed technology relates generally to compositions, methods, and system for utilizing 1-methylxanthine alone and in combination for use in providing physiological benefits. More particularly, the disclosure relates to 1-methylxanthine and other compounds, whether produced synthetically or derived from natural sources, and use of these compounds to provide physiological benefits, which may vary according to 1-methylxanthine concentration and the presence of synergists and antagonists.

BACKGROUND

Caffeine is a bitter, white crystalline purine, a methylxanthine alkaloid, and is chemically related to the adenine and guanine bases of deoxyribonucleic acid (DNA) and ribonucleic acid (RNA). It is found in the seeds, nuts, or leaves of several plants native to Africa, East Asia and South America, and helps to protect them against predator insects and to prevent germination of nearby seeds. The most well-known source of caffeine is the coffee bean, a misnomer for the seed of Coffea plants.

Caffeine concentrations in coffee beverages can be quite variable. A standard cup of coffee is often assumed to provide 100 mg of caffeine, but a recent analysis of 14 different specialty coffees purchased at coffee shops in the US found that the amount of caffeine in 8 oz (~240 ml) of brewed coffee ranged from 72-130 mg (McCusker, R. R., Goldberger, B. A. and Cone, E. J. 2003. Caffeine content of specialty coffees. J. Anal. Toxicol., 27: 520-522.). Caffeine in espresso coffees ranged from 58-76 mg in a single shot. Interestingly, the caffeine content of the same type of coffee purchased from the same store on six separate days varied from 130 to 282 mg per 8-oz serving. Many individuals experience problems with sleep, anxiety, and/or jitteriness with caffeine, which may be exacerbated by an unexpectedly high dose.

Thus, there is a need in the art to identify alternative chemical compounds and mixtures thereof that may provide benefits. It is also desirable to provide chemical compounds and mixtures thereof that may be used to provide a variety of benefits, varying by concentration, thus requiring production of fewer materials.

BRIEF SUMMARY

This disclosure relates to the use of a chemical composition comprising 1-methylxanthine, either naturally or synthetically produced, and optionally other chemicals, including 1-methylxanthine congeners or analogs, to provide a plurality of desirable effects. 1-Methylxanthine analogs may include, but are not limited to, caffeine, paraxanthine, methyl caffeine, theobromine, theophylline, liberine and methylliberine, and their variants. Other suitable actives may include one or more ergogenic (e.g., creatine, beta-alanine, betaine, arginine, citrulline) or nootropic (e.g., Alpha-GPC, CDP-Choline, Acetyl-L-Carnitine, Huperzine A, B-12, tyrosine, taurine) compounds such, St John's Wort, sulbutiamine, and the like.

1-methylxanthine exhibits a wide variety of effects depending on dosage. The presence of other ingredients may also modulate its effects. It may be used to improve endurance performance, mood, promote calm and focus, vigor, lipolysis, energy expenditure, exercise performance, and/or decreased appetite. It may also serve as an antioxidant and an anti-inflammatory.

Further disclosed herein is composition for increasing energy in a subject comprising 1-methylxanthine and paraxanthine. In certain embodiments, paraxanthine and 1-methylxanthine are each present in an amount from about 2 mg to about 800 mg. In further embodiments, paraxanthine and 1-methylxanthine are each present in an amount from about amount from 50 mg to about 400 mg.

According to certain embodiments, the composition further comprises one or more active agents selected from L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis, Agmatine sulfate*, Stinging Nettle, Sea Buckthorn, Curcumin, *Cissus* Quadrilangularis, *Boswellia serrata, Wasabia japonica* (wasabi extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, ginseng, *Ginkgo biloba*, siberian ginseng, *Astragalus*, licorice, green tea, *reishi*, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (*Pyroloquinoline quinone*), Ubiquinone(01), *Nicotinamide riboside*, picamilon, Huperzine A (Chinese clubmoss or *Huperzia serrata*, L-dopa, *Mucuna pruriens*, forskolin (*Coleus forskohlli*), 2-(dimethylamino)ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, ginseng, ashwagandha, *Rhodiola*, theanine BCAAs, beta-alanine, fish oil, citrulline, arginine, hydroxy-methyl-butyrate, HICA, balenine, carnosine, anserine and combinations thereof.

In certain embodiments, administration of the composition to a subject produces a synergistic increase in energy relative to the administration of a comparable dose of paraxanthine or 1-methylxanthine alone.

In certain embodiments, 1-methylxanthine and paraxanthine are present at a ratio of about 4:1 to about 1:4.

Further disclosed herein is a method for increasing energy in a subject comprising administering to the subject a composition comprising an effective amount of 1-methylxanthine. In certain implementations, the amount of 1-methylxanthine administered is from about 2 mg to about 800 mg.

In certain embodiments, the subject experiences and increase in perception of energy of at least about 5%.

According to further embodiments, the subject experiences a decrease of at least one of anxiety, fatigue, perception of effort, and/or perception of pain.

In certain implementations, the composition administered is substantially free of caffeine. In further implementations, the subject abstains from caffeine during the performance of the method.

Further disclosed herein is a method for improving athletic performance in a subject in comprising administering to the subject a composition comprising an effective amount of 1-methylxanthine.

In exemplary implementations, athletic performance is increased by at least about 10%. In further implementations, the subject experiences and increase in endurance. According to certain embodiments, the composition further comprises paraxanthine in an amount from about 2 mg to about 800 mg and administration of the composition to a subject produces a synergistic increase in athletic performance to the administration of a comparable dose of paraxanthine or 1-methylxanthine alone.

In one embodiment, 1-methylxanthine may be used to modulate stimulants, to provide heightened energy without heightened anxiety or nervousness. There may be variability among individuals, as described herein.

In another embodiment 1-methylxanthine may be used as a mild mood enhancer or relaxant.

In a further embodiment, 1-methylxanthine may be used to promote weight loss by reducing appetite, act as an antioxidant and as an anti-inflammatory. 1-methylxanthine may be used transdermally to enhance one or more of these effects.

In another embodiment, a method of treatment for improving physical performance or energy in an individual is provided. This method involves providing the individual with a composition comprising about 2 mg to about 800 mg of 1-methylxanthine, wherein upon administration of the composition the individual experiences improvement of at least one of endurance performance, mood, promote calm and focus, vigor, lipolysis, energy expenditure, exercise performance, and/or decreased appetite. In another embodiment, a second compound such as caffeine may also be administered in the composition.

While multiple embodiments are disclosed, still other embodiments of the disclosure will become apparent to those skilled in the art from the following detailed description, which shows and describes illustrative embodiments of the disclosed compositions, systems and methods. As will be realized, the disclosed compositions, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause unacceptable adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is substantially free of particles would either completely lack particles, or so nearly completely lack particles that the effect would be the same as if it completely lacked particles. In other words, a composition that is substantially free of an ingredient or element may still actually contain such item as long as there is no measurable effect thereof.

As used herein, the term "synergistic effect" or grammatical variations thereof means and includes a cooperative action encountered in a combination of two or more active compounds in which the combined activity of the two or more active compounds exceeds the sum of the activity of each active compound alone. The term "synergistically effective amount," as used herein, means and includes an amount of two or more active compounds that provides a synergistic effect defined above.

Compositions

Disclosed are compositions comprising 1-methylxanthine (1-Mx) and the related uses thereof. 1-Methylxanthine or 1-Methyl-3H-purine-2,6-dione, is a methyl derivative of xanthine, structurally related to caffeine as well as a metabolite of caffeine which also found through caffeine excretion in humans. In humans and other animals, caffeine is first degraded to either paraxanthine (1,7-dimethylxanthine) or theophylline, and then later, to 1-Methylxanthine. 1-Methylxanthine is observed in nature as a metabolite of caffeine in animals and humans.

1-methylxanthine may be produced synthetically or may be isolated from a natural source or through fermentation. 1-Methylxanthine isolated from such sources may be purified to 95% or greater purity. In certain embodiments, 1-methylxanthine is substantially pure. In certain embodiments, less purification may be used such that 1-methylxanthine accounts for 50%, or less. In some embodiments, it may be preferable to utilize 1-methylxanthine isolated from a natural source which may include other congeners of 1-methylxanthine typically found in 1-methylxanthine sources.

It is therefore an object of the present disclosure to provide compositions including 1-methylxanthine capable of imparting a plurality of positive effects.

It is another object of the present disclosure to provide congeners, derivatives and iterations of 1-methylxanthine and synthetic chemical equivalents of 1-methylxanthine.

It is another object of the present disclosure to provide agglomerated 1-methylxanthine, 1-methylxanthine salts, microencapsulated, liposomal or esterified 1-methylxanthine.

It is another object of the present disclosure to provide 1-methylxanthine combined with glycerides, propylene glycol, polyethylene glycol (PEG), lauroyl macrogol, lauroyl macrogol derivatives and co-crystallization products of 1-methylxanthine.

In certain embodiments, the composition is formulated such that a dose contains 1-methylxanthine ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

In certain embodiments, 1-methylxanthine is combined with one or more additional active ingredients selected from: a group consisting of: gallic acid, (+)-catechin (C), (−)-epicatechin (EC), (+)-gallocatechin (GC), (−)-epigallocatechin (EGC), (+)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, cocrystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (Sadenosylmethionine), ASU (avocado-soybean unsapponifiable fraction), cetyl myristoleate, *Dolichos falcate*, triterpenoids, *Acacia catechu, Andrographis paniculata, Scutalleria baicalensis, Agmatine sulfate*, Stinging Nettle, Sea Buckthorn, Curcumin, *Cissus* Quadrilangularis, *Boswellia serrata, Wasabia japonica* (*wasabi* extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, tocopherols, theophylline, alphayohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, ginseng, *Ginkgo biloba*, siberian ginseng, *Astragalus*, licorice, green tea, *reishi*, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (*Pyroloquinoline quinone*), Ubiquinone(01), *Nicotinamide riboside*, picamilon, Huperzine A (Chinese clubmoss or *Huperzia serrata*, L-dopa, *Mucuna pruriens*, forskolin (*Coleus forskohlli*), 2-(dimethylamino)ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, ginseng, ashwagandha, *Rhodiola*, theanine and combinations thereof.

According to certain embodiments, the composition also includes a 1-methylxanthine congener or 1-methylxanthine analog. In certain implementations, the 1-methylxanthine congener or analog is: 7-methylxanthine, paraxanthine, theobromine, theophylline, liberine, methylliberine, and/or combinations thereof. In certain implementations, the 1-methylxanthine congener or analog is caffeine.

According to certain embodiments where the composition is comprised of 1-methylxanthine and caffeine, the effective dose of caffeine is lower than the effective dose of caffeine in a composition without 1-methylxanthine.

Further disclosed herein is a composition comprising paraxanthine and 1-methylxanthine. In exemplary implementations, the composition is formulated such that a dose contains paraxanthine ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

In certain embodiments, 1-methylxanthine and paraxanthine are present in about equal amounts. In these embodiments, 1-methylxanthine and paraxanthine each comprise about 50% of the combined weight of 1-methylxanthine and paraxanthine within the composition, on a w/v basis. In certain further embodiments, the range may be from at least 10% of paraxanthine to 90% and 90% of 1-methylxanthine to 10%, respectively. In further embodiments, 1-methylxanthine and paraxanthine are present at a ratio of about 4:1 to about 1:4.

Further disclosed herein is a composition comprising paraxanthine and 7-methylxanthine. In certain embodiments, the composition is formulated such that a dose contains 7-methylxanthine and paraxanthine each ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

In certain embodiments, 7-methylxanthine and paraxanthine are present in about equal amounts. In these embodiments, 7-methylxanthine and paraxanthine each comprise about 50% of the combined weight of 7-methylxanthine and paraxanthine within the composition, on a w/v basis. In certain further embodiments, the range may be from at least 10% of paraxanthine to 90% and 90% of 7-methylxanthine to 10%, respectively.

Further disclosed herein is a composition comprising 1-methylxanthine and 7-methylxanthine. In certain embodiments, the composition is formulated such that a dose contains 1-methylxanthine and 7-methylxanthine each ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

In certain embodiments, 1-methylxanthine and 7-methylxanthine are present in about equal amounts. In these embodiments, 1-methylxanthine and 7-methylxanthine each comprise about 50% of the combined weight of 1-methylxanthine and 7-methylxanthine within the composition, on a w/v basis. In certain further embodiments, the range may be from at least 10% of 7-methylxanthine to 90% and 90% of 1-methylxanthine to 10%, respectively.

In certain embodiments, the composition is substantially free of caffeine.

Nutritional Supplements

The compositions of the disclosure may take the form of dietary supplements or may themselves be used in combination with dietary supplements, also referred to herein as food supplements.

Nutritional supplements may be found in many forms such as tablets, capsules, soft gels, gel caps, liquids, or powders. Some dietary supplements can help ensure an adequate dietary intake of essential nutrients; others may help reduce risk of disease.

Food Products

The compositions of the disclosure may take the form of a food product. Here, the term "food" is used in a broad sense and covers food and drink for humans as well as food and drink for animals (i.e. a feed). Preferably, the food product is suitable for, and designed for, human consumption.

The food may be in the form of a liquid, solid or suspension, depending on the use and/or the mode of application and/or the mode of administration.

When in the form of a food product, the composition may comprise or be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the compositions of the disclosure may take the form of one of the following: A fruit juice; a beverage comprising whey protein: a health or herbal tea, a cocoa drink, a coffee drink, a yoghurt and/or a drinking yoghurt, a cheese, an ice cream, a desserts, a confectionery, a biscuit, a cake, cake mix or cake filling, a snack food, a fruit filling, a cake or doughnut icing, an instant bakery filling cream, a filling for cookies, a ready-to-use bakery filling, a reduced calorie filling, an adult nutritional beverage, an acidified soy/juice beverage, a nutritional or health bar, a beverage powder, an energy drink, a sublingual, a gummy, a calcium fortified soy milk, or a calcium fortified coffee beverage.

Food Ingredients

Compositions of the present disclosure may take the form of a food ingredient and/or feed ingredient.

As used herein the term "food ingredient" or "feed ingredient" includes a composition which is or can be added to functional foods or foodstuffs as a nutritional and/or health supplement for humans and animals.

The food ingredient may be in the form of a liquid, suspension or solid, depending on the use and/or the mode of application and/or the mode of administration.

Functional Foods

Compositions of the disclosure may take the form of functional foods. As used herein, the term "functional food" means food which is capable of providing not only a nutritional effect but is also capable of delivering a further beneficial effect to the consumer.

Accordingly, functional foods are ordinary foods that have components or ingredients (such as those described herein) incorporated into them that impart to the food a specific function—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Medical Foods

Compositions of the present disclosure may take the form of medical foods. By "medical food" it is meant a food which is formulated to be consumed or administered with or without the supervision of a physician and which is intended for a specific dietary management or condition for which distinctive nutritional requirements, based on recognized scientific principles, are established by medical evaluation.

In another embodiment, 1-methylxanthine may be used at lower dosage levels and/or in conjunction with compounds that modulate or antagonize its activity. Such compositions may induce an improved endurance performance, mood, vigor, lipolysis, energy expenditure, exercise performance, and/or decreased appetite, as described further herein.

An advantage of using the invention may be the reduced likelihood that a person develops a tolerance to chemical compositions in accordance with the principles of the invention. That is, a person may not become desensitized to the effects induced.

According to certain aspects, the disclosed 1-methylxanthine containing compositions has at least the following distinct advantages over the administration of compositions containing comparable doses of caffeine. 1-methylxanthine has substantially lower toxicity. 1-methylxanthine has greater stability (e.g. does not lose potency over time to the same extent as caffeine). 1-methylxanthine containing compositions are more potent wake-promoting agent (in certain embodiments, via adenosine receptor antagonism). Further, 1-methylxanthine containing compositions enhance striatal dopaminergic tone. Still further, 1-methylxanthine does not produce sleep rebound. Further, 1-methylxanthine does not produce withdrawal effects upon cessation of use, as frequently occurs with caffeine. Yet further, 1-methylxanthine does not enhance anxiety. Still further, 1-methylxanthine is less bitter than caffeine. Even further, 1-methylxanthine is effective for a larger portion of the population than caffeine.

In another embodiment, 1-methylxanthine may be used at higher dosage levels and/or with synergistic compounds. These compositions may increase a person's basal/resting metabolic rate, increase thermogenesis, decrease appetite, enhance cognitive performance, increase alpha wave brain activity, and/or induce euphoria. Without being bound by theory, the inventors believe that at higher dosage levels, 1-methylxanthine may be noradrenergic and dopaminergic, and may exhibit increased adenosine receptor inhibition.

In another embodiment, 1-methylxanthine is combined with ephedrine, caffeine, salicylic acid or the like. The foregoing combinations may produce a synergistic effect with the stimulating effects of 1-methylxanthine. For example, in certain embodiments, 1-methylxanthine is being combined with much lesser amounts of caffeine in order to modulate the excessive stimulatory effects of caffeine, thereby stabilizing heart rate and other metabolic activity. That is, a combination of 1-methylxanthine and caffeine may result in a composition that imparts the increased focus and energy induced by caffeine, but without the higher heart rate and blood pressure due to modulation of caffeine's effects by 1-methylxanthine. Thus, the combination may result in heightened awareness and calmness without the jitters caffeine may cause.

Further disclosed herein is a caffeine substitute composition for use in foods and/or beverages comprising any of the foregoing compositions. In certain embodiments, the composition does not increase anxiety when administered to a subject relative to a comparable dose of caffeine. In further embodiments, the composition does not create dependence in a subject upon repeated administrations and does not create withdrawal effects in the subject upon cessation of use. In still further embodiments, the composition is less bitter than a comparable dose of caffeine. In yet further embodiments, the composition is less toxic than a comparable dose of caffeine. According to even further embodiments, administration of the composition to a subject results in decreased heart rate, diastolic blood pressure and/or systolic blood pressure relative to administration of a comparable dose of caffeine.

In another embodiment, 1-methylxanthine may be used as a topical agent for incorporation into body creams or lotions to produce a cream or lotion for lightening skin, firming skin, and/or improving skin elasticity. A 1-methylxanthine topical agent may also be used to promote localized transdermal fat loss. 1-methylxanthine may also be used in a cream or lotion to promote localized enhanced metabolism and/or enhanced thermogenesis.

According to further embodiments, 1-methylxanthine is be combined with one or more of analgesics and/or anti-inflammatory agents. In exemplary implementations, 1-methylxanthine is combined with ibuprofen, salicylic acid, anti-inflammatory agents, salicin, fish oil (omega-3 fatty acids and specialized, small lipid pro-resolving derivatives), tart cherry, hill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, curcumin, tetrahydrocurcumin, ginger, cayenne, white willow bark, *Boswellia serrata*, garlic, vitamin c, cat's claw, devils claw, quercetin and/or triterpenoids.

In another embodiment, 1-methylxanthine is combined with one or more bioavailability enhancers. In exemplary embodiments, bioavailability enhancers include, but are not limited to: bioperine, piperine, black pepper, bergamottin, dihydroxybergamottin (CYP3A4 inhibitors), flavonoids (including hesperidin, naringin, tangeritin, quercetin and nobiletin both in isolation and in combination), pterostilbenes, fisetin, nanoencapsulation, microencapsulation, liposomes and/or phytosomes. The particular enhancers combined with 1-methylxanthine may depend on which qualities of 1-methylxanthine are desired for a particular use.

In another embodiment, the disclosed compositions may be administered using one or more delivery methods, including, for example transdermal patches and/or creams, ready to mix powders, intravenous methods, capsules, tablets, liquid (including liquids for mixing with other beverages), softgels, shot format, gum, and/or cosmetic applications including soaps, lotions and shampoos. 1-methylxanthine's anti-inflammatory qualities may be desired for a variety of topical applications.

Methods of Use

In certain embodiments, 1-methylxanthine may be combined with one or more other chemical compounds (e.g. other active ingredients), to provide a plurality of positive effects in a subject. By altering the dosage of 1-methylxanthine and/or chemical compounds it is combined with, various physiological effects may be selected for. The compositions may provide primarily a single benefit or may provide multiple benefits simultaneously. Depending upon the subject to be treated and the route of administration, the compounds of the invention may be administered at varying doses. Although doses will vary from subject to subject, suitable daily doses are in the range of about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein) per subject, administered in single or multiple doses.

Advantageously, compositions of the present disclosure may be administered in single doses, e.g. once daily or more seldom, or in a total daily dosage administered in divided doses of two, three or four times daily. In certain embodiments, the composition is administered as needed (e.g., when the subject is in need of enhance energy, athletic or cognitive performance or the like).

Athletic Performance

Further disclosed herein is a method for enhancing performance or energy in subject, comprising administering to the subject a composition disclosed herein. As used herein the term "enhancing performance" is intended to mean any improvement in performance. Performance can be assessed in any manner. Certain enhancements are readily measured. For example, in a timed-event, an improved time can assess an enhanced performance. Certain performance enhancing properties can be judged subjectively by the athlete or performer or an observer. In these instances, an enhanced performance means that the performance was perceived subjectively to be improved, magnified, faster, better and the like. In certain embodiments, the disclosed methods are used to enhance athletic performance. "Athletic performance" refers to any professional or recreational activity wherein the performer, for example an athlete, exerts a physical act, such as running, swimming, golf, bowling, archery, football, baseball, basketball, soccer, hiking, cycling, dancing and the like. In certain athletic performance is improved through in improvement of endurance in the subject. In other words, administration of the disclosed compositions improves a subject's level of endurance, thereby enhancing the subject's athletic performance. In further embodiments, administration of the composition to the subject increases cognitive performance which thereby improves athletic performance.

In certain embodiments, upon administration of the composition, the subject experiences improvement of at least one of mood, energy, focus, concentration or sexual desire or a reduction of at least one of anxiety, fatigue, perception of effort or perception of pain.

In further embodiments, upon continued administration to the subject, the composition does not create dependence in the subject and/or withdrawal effect in the subject when continued use is ceased.

Further disclosed herein is a method of increasing athletic endurance in a subject comprising administering to the subject a composition disclosed herein. In certain implementations, the composition administered to the subject comprises 1-methylxanthine and paraxanthine. In exemplary implementations, the administration of paraxanthine and 1-methylxanthine produce a synergistic increase athletic endurance in the subject, relative to the administration of paraxanthine or 1-methylxanthine alone.

According to further embodiments, administration of the disclosed composition to the subject increases the subject's perceived level of energy. In exemplary implementations, the subject experiences an increase in energy of at least about 5 percent. According to certain embodiments, the composition administered further comprises (in addition to 1-Mx and/or paraxanthine) at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum,* tetrahydrocurcumin, and *Solanum asperum* and/or combinations thereof, caffeine, theobromine, naringin, hesperidin, 2-(dimethylamino)ethanol (DMAE), DMAE bitartrate, huperzine A, theacrine, methylliberine, B12, sulbutiamine, *Magnolia* bark, ketones, MCTs, omega 3's, lutein, zeaxanthin, tyrosine and n-acetyl-tyrosine, taurine, acetyl-1-carnitine and/or combinations thereof.

In certain embodiments, the subject's perceived level of energy is increased by between about 2% and about 50%. In further embodiments, the subject's perceived level of energy is increased by between about 5% and about 30%. In yet further embodiments, the subject's perceived level of energy is increased by between about 10% and about 25%.

Muscle Function

Further disclosed herein is a method for increasing muscle function in a subject by administering to the subject a composition disclosed herein. In certain aspects, disclosed herein are methods to promote muscle growth through the administration of an effective amount of one or more compositions disclosed herein. In certain further aspects, administration of effective amounts of the disclosed compositions results in greater level of muscle protein synthesis (MPS) in the subject. In still further aspects, administration of effective amounts of the disclosed compositions results in improved muscle accretion in the subject.

In certain aspects, disclosed herein are methods to promote muscle growth through the administration of an effective amount of one or more compositions disclosed herein. In certain further aspects, administration of effective amounts of the disclosed compositions results in greater level of muscle protein synthesis (MPS) in the subject. In still further aspects, administration of effective amounts of the disclosed compositions results in improved muscle accretion in the subject.

According to certain embodiments, compositions disclosed herein may be administered in conjunction with a strength training regime. As will be appreciated by a person having skill in the art, administration of effective amounts of the disclosed compositions results in improved strength and improved athletic performance/ergogenesis in the subject.

In one aspect, the disclosed compounds inhibit muscle atrophy. In a further aspect, the disclosed compounds increase muscle mass. In a still further aspect, the disclosed compounds induce muscle hypertrophy. In a yet further aspect, the disclosed compounds inhibit of muscle atrophy and increase muscle mass. In an even further aspect, the disclosed compounds inhibit of muscle atrophy and induce muscle hypertrophy. In a further aspect, the inhibition of muscle atrophy is in a subject. In an even further aspect, the increase in muscle mass is in a subject. In a still further aspect, the subject is a mammal. In a yet further aspect, the mammal is a human.

In certain aspects, administration of the disclosed compositions is effective at preventing or treating age-related muscle atrophy or sarcopenia. In further aspects, administration of the disclosed compositions is effective at preventing or treating muscle atrophy associated with muscle immobilization, such as that which frequently occurs with casting of fractured bones. In further aspects, administration of the disclosed compositions is effective at preventing or treating muscle atrophy associated with disease, such as cancer, also known as cachexia.

According to certain aspects the composition is administered to a subject that has sarcopenia. In various aspects, the composition is administered in a therapeutically effective amount. In further aspects, the composition is administered at prophylactically effective amount, (e.g. to a subject at risk for developing sarcopenia, cachexia, or immobilization induced atrophy).

In certain aspects, the composition further comprises one or more additional active ingredient to further enhance muscle strength, size, and/or muscle function. In certain embodiments, the one or more additional active ingredient is an amino acid. According to certain embodiments, the amino acid is selected from a group of branched-chain amino acids (BCAA), including, but not limited to, isoleucine, leucine, and valine. In further embodiments, the amino acid is selected from the group of essential amino acids, including, but not limited to, histidine, isoleucine, leucine, lysine, methionine, phenylalanine, threonine, tryptophan, and valine. In still further embodiments, the amino acid is selected from the group of conditionally essential amino acids including, but not limited to, arginine, cysteine, glutamine, glycine, proline, ergothioneine, and tyrosine. According to the certain embodiments, the conditionally essential amino acid is tyrosine. In still further embodiments, the amino acid is selected from the group of non-essential amino acids including, but not limited to, alanine, aspartic acid, asparagine, glutamic acid, serine, selenocysteine and pyrrolysine. In yet further embodiments, the amino acid derivative is selected from the group of creatine, carnitine, beta-alanine, taurine, beta-hydroxy beta-methylbutyrate L-Arginine, omega-3 fatty acids, Vitamin D, whey protein, BAIBA, and other protein extracts from animal, plant or fermentation sources.

According to exemplary aspects of these embodiments, that may reduce fatigue, improve energy, increase mobility, and improve alertness. In further embodiments, administration of the disclose compositions is cardio protective. In further embodiments, administration of the disclose compositions improves muscle contractions and muscle performance. In exemplary aspects, of these embodiments, muscle performance is enhanced through increasing potassium (K+) transport into skeletal muscle. In further aspects, muscle performance is enhanced through increasing intracellular calcium (e.g., via ryanodine receptor (RyR) activation).

In certain aspects of the foregoing embodiments wherein the composition comprises effective amounts of 1-methylxanthine and paraxanthine, the administration of paraxanthine and 1-methylxanthine produce a synergistic increase in muscle size and/or function in the subject, relative to the administration of paraxanthine or 1-methylxanthine alone.

Weight Loss

According to certain embodiments, fat loss is promoted through inducing thermogenesis in the subject. According to exemplary implementations of these embodiments, the composition may also include one or more compounds selected from: caffeine, green tea, capsaicin, *Garcinia cambogia*, yohimbine, catechols, epigallocatechin gallate EGCG, catechins, and proanthocyanidins and octacosanol, Synephrine, theacrine, methylliberine, cayenne, grains of paradise, ginger extract, and bitter orange.

According to further embodiments, fat loss is promoted through suppression of appetite in the subject. In exemplary implementations of these embodiments, the composition further may include one or more compounds selected from: fenugreek, glucomannan, gymnema sylvestre, 5-HTP, *Caralluma fimbriata*, green tea extract, Conjugated linoleic acid, *Garcinia cambogia*, and *Yerba mate*.

According to still further embodiments, fat loss is promoted through enhancing lipolysis in the subject. In exemplary implementations of these embodiments, the composition further may include one or more compounds selected from caffeine, green tea extract, L-carnitine, *Garcinia cambogia* (hydroxycitric acid), capsaicin, ginseng, taurine, silk peptides, BAIBA, grains of paradise, ginger and octacosanol.

In certain embodiments, the disclosed composition, when administered to a subject, increases the subjects resting energy expenditure, relative to the subject's baseline level or following administration of a placebo. In certain embodiments, the increase in the subject's resting energy expenditure following administration of the disclosed compositions is from about 3% to about 30%. In further embodiments, increase in the subject's resting energy expenditure following administration of the disclosed compositions is from about 5% to about 25%. In yet further embodiments increase in the subject's resting energy expenditure following administration of the disclosed compositions is from about 8% to about 20%. In still further embodiments, increase in the subject's resting energy expenditure following administration of the disclosed compositions is from about 10%.

According to certain implementations, the disclosed method further comprises restricting calorie intake of the subject. In exemplary implementations, the amount of fat loss in the subject is greater than that for a subject with an equivalent calorie restriction that has not been provided the composition. According to further implementations, the ratio of fat loss to muscle loss in the subject the subject is greater than that for a subject with an equivalent calorie restriction that has not been provided the composition.

Further disclosed herein are methods for suppressing appetite in a subject by administering to the subject a composition comprising about 2 mg to about 800 mg of paraxanthine. In certain embodiments, administration of the composition to the subject reduces the subject's appetite by from 5% to about 70%. In further embodiments, reduction of the subject's appetite is from about 10% to about 60%. In yet further embodiments, reduction of the subject's appetite is from about 20% to about 50%. In still further embodiments, reduction of the subject's appetite is at least about 30%.

According to certain embodiments of the disclosed method, the composition is administered in a therapeutically effective amount. In further embodiments, the composition is administered in a prophylactically effective amount.

In certain aspects, disclosed herein are methods to promote weight loss through the administration of an effective amount of one or more compositions disclosed herein. According to certain aspects, administration of effective amounts of the disclosed compositions are used in treating diabetes mellitus; preventing, slowing progression of, delaying or treating of a condition or disorder selected from the group consisting of complications of diabetes mellitus; preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity, metabolic syndrome and gestational diabetes; or improving glycemic control and/or for reducing of fasting plasma glucose, of postprandial plasma glucose and/or of glycosylated hemoglobin HbA1c; or preventing, slowing, delaying or reversing progression from impaired glucose tolerance IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischemia, arteriosclerosis, myocardial infarction, stroke and peripheral arterial occlusive disease; or reducing body weight and/or body fat or preventing an increase in body weight and/or body fat or facilitating a reduction in body weight and/or body fat; or preventing, slowing, delaying or treating diseases or conditions attributed to an abnormal accumulation of ectopic fat; or maintaining and/or improving the insulin sensitivity and/or for treating or preventing hyperinsulinemia and/or insulin resistance; preventing, slowing progression of, delaying, or treating new onset diabetes after transplantation (NODAT) and/or post-transplant metabolic syndrome (PTMS); preventing, delaying, or reducing NODAT and/or PTMS associated complications including micro- and macrovascular diseases and events, graft rejection, infection, and death; treating diabetes associated with cystic fibrosis treating hyperuricemia and hyperuricemia associated conditions; treating or prevention kidney stones; treating hyponatremia; in a patient in need thereof.

Another aspect encompasses a combination therapy to regulate fat storage, energy utilization, and/or weight loss in a subject. In an exemplary embodiment, a combination for increasing energy utilization, decreasing body fat or for promoting weight loss may include combining the methods and compositions disclosed with a procedure or therapy such as a pharmaceutical therapy, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, brown adipose tissue modulation (e.g., controlled activation, enhanced differentiation, supplemental implantation, etc.), cryolipolysis, pharmaceutical administration, electrical stimulation of nerves that innervate at least a portion of the gastrointestinal tract, therapies impacting circadian rhythms, bile acid modulation, intestinal mucus production and metabolism, duodenal endoluminal barrier or similar manipulations of the gastrointestinal tract. For example, a composition dileucine can be administered to the subject prior to, concurrently with or after a gastric bypass or other gastrointestinal or bariatric procedure.

In certain aspects, administration of the disclosed compositions is effective at preventing reducing body weight and/or body fat or preventing an increase in body weight and/or body fat or facilitating a reduction in body weight and/or body fat; or preventing, slowing, delaying or treating diseases or conditions attributed to an abnormal accumulation of liver fat; or maintaining and/or improving the insulin sensitivity and/or for treating or preventing hyperinsulinemia and/or insulin resistance.

Cognitive Function

Disclosed herein is a method of enhancing cognitive function in a subject comprising administering to the subject a composition disclosed herein. In certain embodiments, improved cognitive function is measured by an increase in one or more of: attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

In certain embodiments, administration of the disclosed composition increases working memory.

In further embodiments, administration of the disclosed composition increases attention.

According to certain embodiments, composition of the instantly disclosed methods to enhance cognitive function further comprise tyrosine, N-acetyl-tyrosine, taurine, huperzine A, acetyl-1-carnitine, CDP choline, Alpha GPC, choline bitrate, choline citrate, B12, caffeine, methyllliberine, theacrine, paraxanthine, theobromine, ashwagandha, *Rhodiola*, lutein, zeaxanthin, fish oil, creatine, ginseng, lions mane, niacin, cordyceps, theanine, B-vitamins, GABA, sulbutiamine, vinpocetine, adenosine triphosphate, inositol, enhanced arginine silicate, nitrates, electrolytes, hesperidin and derivatives of hesperidin and/or *Bacopa*.

In certain embodiments, the subject has experience age-related cognitive decline. In exemplary implementations, administration of the composition to the subject increases the level BDNF in the subject. According to certain embodiments, administration of the composition to the subject increases brain derived neurotrophic factor (BDNF) levels in the subject. In exemplary implementations, BDNF levels are increased by from about 5% to about 40%. In further embodiments, BDNF levels are increased by at least about 15%. In further embodiments, administration of the composition to the subject increases other neurotrophic factors such as neuronal growth factor (NGF). In still further embodiments, administration of the composition to the subject increases levels of mTOR in the CNS.

Methods of Treatment

Further disclosed herein is a method of treating a condition in a subject in need thereof by administering to the subject a composition disclosed herein. In certain embodiments, the condition is selected from narcolepsy, epilepsy, attention deficit disorders, attention deficit hyperactivity syndrome (ADHD), cognitive deficit disorders, palsies, uncontrolled anger, migraine, substance abuse addictions, eating disorders, depression, anxiety disorders, traumatic head injury (TBI), Parkinson's disease, Alzheimer's, and dementia.

Further disclosed herein is a method for treating a mood disorder by administering to a subject in need thereof a composition disclosed herein. In certain embodiments, the mood disorder is selected from clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, comorbid depression, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein.

In certain embodiments, the mood disorder is depression. In exemplary implementations, subject has been diagnosed with depression or is at risk of depression.

Further disclosed herein is a method for treating an anxiety disorder in a subject in need thereof by administering to a subject in need thereof a composition disclosed herein. In certain embodiments, the anxiety disorder is selected from: generalized anxiety disorder, panic disorder, obsessive compulsive disorder, phobia, post-traumatic stress disorder). As will be appreciated by those skilled in the art, anxiety disorder is a blanket term covering several different forms of abnormal and pathological fear and anxiety.

According to certain embodiments, the composition is administered in a therapeutically effective amount. In further embodiments, the composition is administered in a prophylactically effective amount.

In certain embodiments, the composition used in the method of treating a mood disorder or anxiety disorder further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum,* tetrahydrocurcumin, and *Solanum asperum* and/or combinations thereof, caffeine, theobromine, naringin, hesperidin, 2-(dimethylamino) ethanol (DMAE), DMAE bitartrate, *Magnolia* bark, theanine, phosphatidylserine, ashwagandha, *Rhodiola*, taurine, tyrosine, n-acetyl-tyrsoine, macuna, *Sceletium tortuosa*, 5-HTP, tryptophan, saffron, Vitamin D, SAMe, lions mane and/or huperzine A.

Further disclosed herein is a method for treating or preventing age-related cognitive decline in a subject in need thereof, comprising administering to the subject an effective amount of a composition disclosed herein. In certain embodiments, administration of the composition increases one or more of attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition. In certain implementations, administration of the composition to the subject increases levels of catalase and/or glutathione in the subject. In further implementations, the composition administered to the subject comprises paraxanthine and 1-methylxanthine and the administration of paraxanthine and 1-methylxanthine produce a synergistic increase in catalase and/or glutathione in the subject, relative to the administration of paraxanthine or 1-methylxanthine alone.

According to still further embodiments, administration of the composition to the subject increases BDNF in the subject. In further implementations, the composition administered to the subject comprises paraxanthine and 1-methylxanthine and the administration of paraxanthine and 1-methylxanthine produce a synergistic increase in BDNF in the subject, relative to the administration of paraxanthine or 1-methylxanthine alone.

According to further embodiments, administration of the composition to the subject decreases the level of amyloid β-protein (Aβ) in the subject. In exemplary implementations, administration of paraxanthine and 1-methylxanthine produce a synergistic decrease in Aβ in the subject, relative to the administration of paraxanthine or 1-methylxanthine alone.

Further disclosed herein is a method for treating or preventing Alzheimer's disease in subject in need thereof, comprising administering to the subject an effective amount of a composition disclosed herein. In certain implementations, administration of the composition to the subject decreases the level of amyloid β-protein (Aβ) in the subject. In exemplary implementations, administration of paraxanthine and 1-methylxanthine produce a synergistic decrease in Aβ in the subject, relative to the administration of paraxanthine or 1-methylxanthine alone. In certain embodiments, subject has been diagnosed with Alzheimer's disease.

In further embodiments, the subject is at risk of Alzheimer's disease. In yet further embodiments, the subject has been diagnosed with mild cognitive impairment.

According to certain embodiments, the composition disclosed herein are used in the treatment of one or more medical conditions in a subject in need thereof. In certain implementations, the disclosed composition is administered to a subject suffering from narcolepsy, sleep apnea, and shift work sleep disorder, insomnia epilepsy, attention deficit disorders, attention deficit hyperactivity syndrome (ADHD), cognitive deficit disorders, palsies, uncontrolled anger, migraine, substance abuse addictions, eating disorders, depression, anxiety disorders, traumatic head injury (TBI), Parkinson's disease, Alzheimer's, and/or dementia.

In certain aspects, the disclosed compositions are a neuroprotective agent. In certain embodiments, administration of the disclosed compositions to a subject in need thereof is neuroprotective. In exemplary aspects of these embodiments, this neuroprotection is in the form of protecting against dopaminergic cell death.

According to further embodiments, disclosed compositions are useful for the treatment of geriatric depression. In exemplary embodiments, the compositions are effective in treating subjects suffering from geriatric depression an essential, vascular or traumatic origin. And of the mental decay in the elderly.

The administration of the disclosed compositions to a subject may include any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, intradermal administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Various aspects and embodiments of the present invention are defined by the following numbered clauses:

1. A composition comprising a first active ingredient comprising about from 2 mg to about 800 mg 1-methylxanthine.
2. The composition of clause 1, wherein 1-methylxanthine is present in amount from about 20 mg to about 600 mg.
3. The composition of clause 2, wherein 1-methylxanthine is present in amount from 50 mg to about 400 mg.
4. The composition of clauses 1-3, further comprising a second active ingredient, selected from a group consisting of: L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis, Agmatine sulfate*, Stinging Nettle, Sea Buckthorn, Curcumin, *Cissus* Quadrilangularis, *Boswellia serrata, Wasabia japonica* (*wasabi* extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, ginseng, *Ginkgo biloba*, siberian ginseng, *Astragalus*, licorice, green tea, *reishi*, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (*Pyroloquinoline quinone*), Ubiquinone(01), *Nicotinamide riboside*, picamilon, Huperzine A (Chinese clubmoss or *Huperzia serrata*, L-dopa, *Mucuna pruriens*, and forskolin (*Coleus forskohlli*), 2-(dimethylamino) ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, ginseng, ashwagandha, *Rhodiola*, theanine BCAAs, beta-alanine, fish oil, citrulline, arginine, HMB, HILA, balenine, carnosine, anserine and combinations thereof.
5. The composition of clause 1, further comprising a 1-methylxanthine congener or 1-methylxanthine analog.
6. The composition of clause 5, wherein said 1-methylxanthine congener or analog is selected from the group consisting of caffeine, 7-methylxanthine, 3-methylxanthine, paraxanthine, theobromine, theophylline, liberine, methylliberine, and combinations thereof.
7. The composition of clause 6, wherein the 1-methylxanthine congener or analog is caffeine.
8. The composition of clause 7, wherein the effective dose of caffeine is lower than the effective dose of caffeine in a composition without 1-methylxanthine.
9. A composition comprising paraxanthine and 1-methylxanthine.
10. The composition of clause 9, wherein the paraxanthine and 1-methylxanthine are each present in an amount from about 2 mg to about 800 mg.

11. The composition of clause 10, wherein the paraxanthine and 1-methylxanthine are each present in an amount from about 20 mg to about 600 mg.
12. The composition of clause 11, wherein the paraxanthine and 1-methylxanthine are each present in an amount from about amount from 50 mg to about 400 mg.
13. The composition of any of clauses 9-12, further comprising one or more of an active selected from a group consisting of: L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis, Agmatine sulfate*, Stinging Nettle, Sea Buckthorn, Curcumin, *Cissus* Quadrilangularis, *Boswellia serrata, Wasabia japonica* (*wasabi* extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, flavenoids, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, ginseng, *Ginkgo biloba*, siberian ginseng, *Astragalus*, licorice, green tea, *reishi*, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (*Pyroloquinoline quinone*), Ubiquinone(01), *Nicotinamide riboside*, picamilon, Huperzine A (Chinese clubmoss or *Huperzia serrata*, L-dopa, *Mucuna pruriens*, and forskolin (*Coleus forskohlli*), 2-(dimethylamino) ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, ginseng, ashwagandha, *Rhodiola*, theanine BCAAs, beta-alanine, fish oil, citrulline, arginine, HMB, HILA, balenine, carnosine, anserine and combinations thereof.
14. A composition comprising 1-methylxanthine and 7-methylxanthine.
15. The composition of clause 14, wherein the 1-methylxanthine and 7-methylxanthine are each present in an amount from about 2 mg to about 800 mg.
16. The composition of clause 15, wherein the 1-methylxanthine and 7-methylxanthine are each present in an amount from about 20 mg to about 600 mg.
17. The composition of clause 16, wherein the 1-methylxanthine and 7-methylxanthine are each present in an amount from about amount from 50 mg to about 400 mg.
18. The composition of any of clauses 14 to 17, further comprising one or more active ingredient, selected from a group consisting of: L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis, Agmatine sulfate*, Stinging Nettle, Sea Buckthorn, Curcumin, *Cissus* Quadrilangularis, *Boswellia serrata, Wasabia japonica* (*wasabi* extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, ginseng, *Ginkgo biloba*, siberian ginseng, *Astragalus*, licorice, green tea, *reishi*, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (*Pyroloquinoline quinone*), Ubiquinone(01), *Nicotinamide riboside*, picamilon, Huperzine A (Chinese clubmoss or *Huperzia serrata*, L-dopa, *Mucuna pruriens*, and forskolin (*Coleus forskohlli*), 2-(dimethylamino) ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, ginseng, ashwagandha, *Rhodiola*, theanine BCAAs, beta-alanine, fish oil, citrulline, arginine, hydroxy-methyl-butyrate, HICA, balenine, carnosine, anserine, carbonate, probiotic, and combinations thereof.

19. The composition of any preceding clause, wherein the is a powder.

20. The composition of any preceding clause, wherein the supplement is in a solid oral dosage form.

21. The composition of any preceding clause, wherein the supplement is formulated for topical administration.

22. The method of any preceding clause, except clauses 7-8, wherein the composition is substantially free of caffeine.

23. A method for improving energy in subject, comprising: administering to the subject with the composition of clauses 1-21.

24. The method of clause 23, wherein upon administration of the composition, the subject experiences improvement of at least one of mood, energy, focus, concentration or sexual desire or a reduction of at least one of anxiety, fatigue, perception of effort or perception of pain.

25. The method of clause 24, wherein upon continued administration to the subject, the composition does not create dependence in the subject and/or withdrawal effect in the subject when continued use is ceased.

26. The method of clause 23, wherein the amount of 1-methylxanthine provided is from about 50 mg to about 400 mg.

27. The method of clause 23, wherein the subject experiences a decrease in fatigue of at least about 6 percent.

28. The method of clause 23, wherein the subject experiences an increase in energy of at least about 5 percent.

29. The method of clause 23, wherein the composition further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, *Magnolia* bark, theanine, phosphatidylserine, ashwagandha, *Rhodiola*, taurine, tyrosine, n-acetyl-tyrsoine, macuna, *Sceletium tortuosa*, 5-HTP, tryptophan, saffron, Vitamin D, SAMe, lions mane and huperzine A.

30. A method of increasing athletic endurance in a subject comprising administering to the subject the composition of any of clauses 1-13.

31. The method of clause 30, wherein the composition is the composition of any of clauses 9-13, and wherein the administration of paraxanthine and 1-methylxanthine produce a synergistic increase athletic endurance in the subject, relative to the administration of paraxanthine or 1-methylxanthine alone.

32. A method of treating a condition in a subject in need thereof, comprising administering to the subject the composition of any of clauses 1-13.

33. The method of clause 32, wherein the condition is selected from narcolepsy, epilepsy, attention deficit disorders, attention deficit hyperactivity syndrome (ADHD), cognitive deficit disorders, palsies, uncontrolled anger, migraine, substance abuse addictions, eating disorders, depression, anxiety disorders, traumatic head injury (TBI), concussion, Parkinson's disease, Alzheimer's, and dementia.

34. The method of clause 32, wherein the condition is a mood disorder.

35. The method of clause 34, wherein the mood disorder is depression.

36. The method of clause 35, wherein the subject has been diagnosed with depression or is at risk of depression.

37. The method of clause 33, wherein the condition is an anxiety disorder.

38. The method of clause 33, wherein the composition is administered in a therapeutically effective amount.

39. The method of clause 33, wherein the composition is administered in a prophylactically effective amount.

40. The method of clause 33, wherein the composition comprises 1-methylxanthine at an amount from about 2 mg to about 800 mg.

41. The method of clause 32, wherein the composition further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, *Magnolia* bark, theanine, phosphatidylserine, ashwagandha, *Rhodiola*, taurine, tyrosine, n-acetyl-tyrsoine, macuna, *Sceletium tortuosa*, 5-HTP, tryptophan, saffron, Vitamin D, SAMe, lions mane and/or huperzine A.

42. A method of enhancing attention in a subject in need thereof comprising administering the composition of any of clauses 1-13.

43. A method of improving working memory in a subject in need thereof comprising administering a composition to the subject comprising the composition of any of clauses 1-13.

44. A method of improving cognitive performance in a subject comprising administering the composition of any of clause 1-13.

45. The method of clause 44, wherein improved cognitive function is measured by an increase in one or more of: attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

46. The method of clause 44-45, wherein the subject has experience age-related cognitive decline.

47. The method clauses 44-46, wherein administration of the composition to the subject increases the level BDNF in the subject.

48. A method for treating or preventing age-related cognitive decline in a subject in need thereof, comprising administering to the subject an effective amount of the composition of any of clauses 1-13.

49. The method of clause 48, wherein administration of the composition increases one or more of attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

50. The method of clause 49, wherein administration of the composition to the subject increases levels of catalase and/or glutathione in the subject.

51. The method of clause 50, wherein the composition is the composition of any of clauses 9-13, and wherein the administration of paraxanthine and 1-methylxanthine produce a synergistic increase in catalase and/or glutathione in the subject, relative to the administration of paraxanthine or 1-methylxanthine alone.

52. The method of clause 49, wherein administration of the composition to the subject increases BDNF in the subject.

53. The method of clause 51, wherein the composition is the composition of any of clauses 9-13, and wherein the administration of paraxanthine and 1-methylxanthine produce a synergistic increase in BDNF in the subject, relative to the administration of paraxanthine or 1-methylxanthine alone.

54. The method of clause 49, wherein administration of the composition to the subject decreases the level of amyloid β-protein (Aβ) in the subject.

55. The method of clause 54, wherein administration of the composition is the composition of any of clauses 9-13, and wherein the administration of paraxanthine and 1-methylxanthine produce a synergistic decrease in Aβ in the subject, relative to the administration of paraxanthine or 1-methylxanthine alone.

56. A method for treating or preventing Alzheimer's disease in subject in need thereof, comprising administering to the subject an effective amount of the composition of any of clauses 1-13.

57. The method of clause 56, wherein administration of the composition is the composition of any of clauses 9-13, and wherein the administration of paraxanthine and 1-methylxanthine produce a synergistic decrease in Aβ in the subject, relative to the administration of paraxanthine or 1-methylxanthine alone.

58. The method of clause 56, wherein the subject has been diagnosed with Alzheimer's disease.

59. The method of clause 56, wherein the subject is at risk of Alzheimer's disease.

60. The method of clause 56, wherein the subject has been diagnosed with mild cognitive impairment.

61. A caffeine substitute composition for use in a dietary supplement comprising the composition of any of clauses 1-13.

62. The composition of clause 61, wherein the composition does not increase anxiety when administered to a subject relative to a comparable dose of caffeine.

63. The composition of clause 61, wherein the composition does not create dependence in a subject upon repeated administrations and does not create withdrawal effects in the subject upon cessation of use.

64. The composition of clause 61, where the composition is less bitter than a comparable dose of caffeine.

65. The composition of clause 61, where the composition is less toxic than a comparable dose of caffeine.

66. The composition of clause 61, wherein the administration of the composition to a subject results in decreased heart rate, diastolic blood pressure and/or systolic blood pressure relative to administration of a comparable dose of caffeine.

67. A method for increasing muscle function in a subject, comprising: administering to the subject the composition of any of clauses 1-13.

68. The method of clause 67, wherein the composition further comprises one or more compounds selected from the list consisting of: isoleucine, leucine, and valine, histidine, isoleucine, leucine, lysine, methionine, phenylalanine, threonine, tryptophan, valine, creatine, arginine, cysteine, glutamine, glycine, proline, tyrosine, carnitine, beta-alanine, taurine, and beta-hydroxy beta-methylbutyrate.

69. A nutritional supplement for improving muscle strength, muscle size, and/or muscle function comprising the composition of any of clauses 1-13.

70. The nutritional supplement of clause 69, wherein the nutritional supplement is powder or a capsule.

71. The nutritional supplement of clause 69, wherein the nutritional supplement is a functional food.

72. The nutritional supplement of clause 71, wherein the functional food is a beverage, nutrition bar, yoghurt, or cereal.

73. The nutritional supplement clause 69, further comprises one or more compounds selected from the list consisting of: isoleucine, leucine, and valine, histidine, isoleucine, leucine, lysine, methionine, phenylalanine, threonine, tryptophan, valine, creatine, arginine, cysteine, glutamine, glycine, proline, tyrosine, carnitine, beta-alanine, taurine, beta-hydroxy beta-methylbutyrate, L-arginine, Omega-3 fatty acids, Vitamin D, whey protein, and other protein extracts from animal, plant or fermentation sources.

74. A method of increasing muscle size in a subject comprising administering to the subject in need thereof with an effective amount of the composition of any of clauses 1-13.

75. The method of clause 74, wherein the composition is the composition of any of clauses 9-13, and wherein the administration of paraxanthine and 1-methylxanthine produce a synergistic increase in muscle size in the subject, relative to the administration of paraxanthine or 1-methylxanthine alone.

76. A method for promoting weight loss in a subject, comprising: administering to the subject the composition of any of clauses 1-13.

77. The method of clause 76, wherein weight loss is promoted through inducing thermogenesis in the subject.

78. The method of clause 77, wherein the composition further comprises one or more compounds selected from a list consisting of: caffeine, green tea, capsaicin, *Garcinia cambogia*, yohimbine and bitter orange.

79. The method of clause 76, wherein weight loss is promoted through suppression of appetite in the subject and wherein administration of the composition to the subject suppresses appetite in the subject by at least about 30%.

80. The method of clause 76, wherein weight loss is promoted through enhancing lipolysis in the subject.

81. The method of clause 76, wherein administration of the composition to the subject decreases the respiratory quotient in the subject by at least about 10%.

82. The method of clause 76, wherein resting energy expenditure in the subject is increased by at least about 15%.
83. The method of clause 80, wherein the wherein the composition further comprises one or more compounds selected from a list consisting of caffeine, green tea extract, L-carnitine, *Garcinia cambogia* (hydroxycitric acid), capsaicin, ginseng, taurine, silk peptides, catechols, epigallocatechin gallate (EGCG), catechins, proanthocyanidins and octacosanol.
84. The method of clause 76, further comprising restricting calorie intake of the subject and wherein the amount of weight loss in the subject is greater than that for a subject with an equivalent calorie restriction that has not been provided the composition and wherein the ratio of fat loss to muscle loss in the subject is greater than that for a subject with an equivalent calorie restriction that has not been provided the composition.
85. The method of clause 76, wherein the subject is not administered caffeine.
86. A method for suppressing appetite in a subject comprising: administering to the subject the composition of any of clauses 1-13.
87. The method of clause 86, wherein administration of the composition decreases appetite in the subject by at least about 30%.
88. The method of clause 86, wherein the subject is not administered caffeine.
89. A method for promoting fat loss in subject, comprising: administering to the subject with the composition of any of clauses 1-13.
90. The method of clauses 89, wherein the subject is not administered caffeine.
91. The method of clause 89, wherein fat loss is promoted through inducing thermogenesis in the subject.
92. The method of clause 91, wherein the composition further comprises one or more compounds selected from the list consisting of: caffeine, green tea, capsaicin, *Garcinia cambogia*, yohimbine, catechols, EGCG, catechins, and proanthocyanidins and octacosanol and bitter orange.
93. The method of clause 89, wherein fat loss is promoted through suppression of appetite in the subject.
94. The method of clause 93, wherein administration of the composition to the subject suppresses appetite in the subject by at least about 30%.
95. The method of clause 89, wherein administration of the composition to the subject decreases the respiratory quotient in the subject by at least about 10%.
96. The method of clause 93, wherein the composition further comprises one or more compounds selected from the list consisting of: fenugreek, glucomannan, gymnema sylvestre, 5-HTP, *Caralluma fimbriata*, green tea extract, conjugated linoleic acid, *Garcinia cambogia*, and Yerbamate.
97. The method of clause 89, wherein fat loss is promoted through enhancing lipolysis in the subject.
98. The method of clause 97, wherein the wherein the composition further comprises one or more compounds selected from the list consisting of caffeine, green tea extract, L-carnitine, *Garcinia cambogia* (hydroxycitric acid), capsaicin, ginseng, taurine, silk peptides and octacosanol.
99. The method of clause 89, further comprising restricting calorie intake of the subject.
100. The method of clause 99, wherein the amount of fat loss in the subject is greater than that for a subject with an equivalent calorie restriction that has not been provided the composition.
101. The method of clause 99, wherein the ratio of fat loss to muscle loss in the is greater than that for a subject with an equivalent calorie restriction that has not been provided the composition.
102. A composition for increasing energy in a subject comprising 1-methylxanthine and paraxanthine.
103. The composition of clause 102, wherein the paraxanthine and 1-methylxanthine are each present in an amount from about 2 mg to about 800 mg.
104. The composition of clause 103, wherein the paraxanthine and 1-methylxanthine are each present in an amount from about amount from 50 mg to about 400 mg.
105. The composition of clause 102, further comprising an active agent, selected from a group consisting of: L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, hill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis, Agmatine sulfate*, Stinging Nettle, Sea Buckthorn, Curcumin, *Cissus* Quadrilangularis, *Boswellia serrata, Wasabia japonica* (wasabi extract for Tea Tree Oil), Emu Oil, *Arnica, Mangifera indica* L. (Anacardiaceae), *Lagenaria breviflora, Zingiber officinale* (ginger &gingerols/shogaols), *Hoodia gordonii*, caffeine, yohimbine, methylsynephrine, synephrine, theobromine, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, ginseng, *Ginkgo biloba*, siberian ginseng, *Astragalus*, licorice, green tea, *reishi*, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (*Pyroloquinoline quinone*), Ubiquinone(01), *Nicotinamide riboside*, picamilon, Huperzine A (Chinese clubmoss or *Huperzia serrata*, L-dopa, *Mucuna pruriens*, forskolin (*Coleus forskohlli*), 2-(dimethylamino)ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, ginseng, ashwagandha, *Rhodiola*, theanine BCAAs, beta-alanine, fish oil, citrulline, arginine, hydroxy-methylbutyrate, HICA, balenine, carnosine, anserine and combinations thereof.

106. The composition of clause 102, wherein administration of the composition to a subject produces a synergistic increase in energy relative to the administration of a comparable dose of paraxanthine or 1-methylxanthine alone.

107. The composition of clause 102, wherein 1-methylxanthine and paraxanthine are present at a ratio of about 4:1 to about 1:4.

108. A method for increasing energy in a subject comprising administering to the subject a composition comprising an effective amount of 1-methylxanthine.

109. The method of clause 108, wherein the amount of 1-methylxanthine administered is from about 2 mg to about 800 mg.

110. The method of clause 108, wherein the subject experiences and increase in perception of energy of at least about 5%.

111. The method of clause 108, wherein the subject experiences a decrease of at least one of anxiety, fatigue, perception of effort, and/or perception of pain.

112. The method of clause 108, wherein the composition further comprises paraxanthine in an amount from about 2 mg to about 800 mg.

113. The method of clause 112, wherein the administration of paraxanthine and 1-methylxanthine produce a synergistic increase in perception of energy in the subject, relative to the administration of a comparable dose of paraxanthine or 1-methylxanthine alone.

114. The method of clause 108, wherein the composition further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino)ethanol (DMAE), DMAE bitartrate, *Magnolia* bark, theanine, phosphatidylserine, ashwagandha, *Rhodiola*, taurine, tyrosine, n-acetyl-tyrsoine, macuna, *Sceletium tortuosa*, 5-HTP, tryptophan, saffron, Vitamin D, SAMe, lions mane and huperzine A.

115. The method of clause 108, wherein the composition is substantially free of caffeine.

116. A method for improving athletic performance in a subject in comprising administering to the subject a composition comprising an effective amount of 1-methylxanthine.

117. The method of clause 115, wherein the amount of 1-methylxanthine administered is from about 50 mg to about 400 mg.

118. The method of clause 116, wherein athletic performance is increased by at least about 10%.

119. The method of clause 116, wherein the subject experiences and increase in endurance.

120. The method of clause 116, wherein the composition further comprises paraxanthine in an amount from about 2 mg to about 800 mg and wherein administration of the composition to a subject produces a synergistic increase in athletic performance to the administration of a comparable dose of paraxanthine or 1-methylxanthine alone.

121. The method of clause 116, wherein the composition further comprises at least one agent selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino)ethanol (DMAE), DMAE bitartrate, huperzine A, theacrine, methylliberine, B12, sulbutiamine, *Magnolia* bark, ketones, MCTs, omega 3's, lutein, zeaxanthin, tyrosine and n-acetyl-tyrosine, taurine, acetyl-1-carnitine and/or combinations thereof.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

Sports & Active Nutrition, Athletic Performance, Strength, Endurance, Muscle Mass 1.1. Methods Twenty-four 8-week-old male Swiss Albino mice were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into three groups (n=8 per group in each test) for oral treatment once a day, at approximately same time each day (±1 hour), for 28 consecutive days: (1) vehicle control or (2) 1-methylxanthine or (3) 1-methylxanthine plus paraxanthine. The dose administered to the mice was calculated using US Food and Drug Administration for human equivalence doses (HED), assuming a human weight of 60 kg. The following HED was used in this study: 100 mg 1-methylxanthine (Ingenious Ingredients, L.P Lewisville, TX, USA; mouse dose: 20.5 mg/kg bw/day), or 100 mg 1-methylxanthine (Ingenious Ingredients, L.P Lewisville, TX, USA; mouse dose: 20.5 mg/kg bw/day) plus 100 mg paraxanthine (ENFINITY™, Ingenious Ingredients, L.P Lewisville, TX, USA; mouse dose: 20.5 mg/kg bw/day). 0.5% Carboxy Methyl Cellulose sodium was used as vehicle and the test item formulations were prepared daily. Dosing was conducted via oral gavage using disposable polypropylene syringes with sterilized stainless steel gavage tubes. Food intake was monitored daily while water intake was ad libitum. BW was recorded weekly. Animals were not trained on day 28 with all animals receiving their final dose on day 28 was given 1 hour prior to completing strength and endurance testing. Animals were then kept overnight for fasting and on day 29 the animals were sacrificed for final collection of blood and tissue samples. Thus, all collected tissue samples were deemed to be collected in a basal state.

TABLE 1

Overview of Research Design

| Procedure | Day 1 | Day 28 |
|---|---|---|
| Daily housing of constant temperature and humidity with 12:12 h light-dark cycle | X | X |
| Daily food consumption assessed with standard laboratory diet | X | X |
| Ad libitum water | X | X |
| Oral treatment at same time per day of assigned dose | X | X |
| Forelimb grip strength | X | X |
| Treadmill endurance test | X | X |
| Daily exercise treadmill training for 60 min/day, 5 days week | X | X |
| Final dose 1 hour prior to testing |  | X |
| Euthanized following testing |  | X |
| Excision and weight of liver, heart, gastrocnemius, and sodium |  | X |

1.2. Sample Collection

Animals were not trained on day 28 and were kept for overnight fasting. All animals were euthanized by 95% $CO_2$ after 28 full days of following their assigned treatment. The gastrocnemius was excised and weighed.

1.3. Forelimb Grip Strength Test

The forelimb grip strength was measured on day 0 and day 28 by using a stainless-steel grill to assess muscle strength (Orchid Scientific & Innovative India Pvt Ltd, India). Grip strength was measured one hour after treatment. Briefly, each mouse was first placed in the testing room for ten minutes to acclimate. Each mouse was then placed over the top of the grid of a grip-strength meter to allow the mouse to grasp the grid with all four paws. The mouse was held by the base of the tail without pressing down upon the grid. The animal was then gently pulled backwards away from the grid by the tail pulling along the axis of the grip strength measurement. The speed was slow enough to let the mouse to develop a resistance against the pulling force and the score that is displayed (gf) on the screen of the grip strength measurement was recorded once the mouse released the grid. Each animal performed three independent trials and the mean of the three trials was calculated and recorded.

1.4. Exercise Training

During the treatment period, exercise training was completed using a motorized treadmill (Exer 3/6, Columbus Instruments international, Ohio, USA) at a moderate intensity of 20 cm/sec as maximal running speed, an incline of ten degrees and a shock intensity of 0.2 mA, for ten minutes. The speed of the treadmill was manually adjusted by increasing the belt speed by 5 cm/sec every two minutes throughout the total duration of ten minutes. All animals were adapted to this procedure daily 60 minutes after dosing for five days in a week during the treatment period.

1.5. Treadmill Endurance Test

On 28th day of each respective treatment, all animals were subjected to a muscle endurance test. Muscle endurance was accomplished on a motorized treadmill using speeds that ranged from 5-50 cm/sec, and an incline of ten degrees. Uphill running involves concentric muscle contractions and increases the muscular work compared to running on a flat surface resulting in faster exhaustion. The belt speed started at approximately 15 cm/sec and increased by 5 cm/sec every two minutes until it reached a speed of 50 cm/sec. Animals were subjected to the treadmill test until exhaustion. The points of exhaustion were defined at the time point at which the animals fell down into the shock zone. Distance traveled (cm) was measured as a marker of exercise performance.

2. Results 2.1. 1-Methylxanthine 2.1.1. Effect of Supplementation on Forelimb Grip Strength Forelimb grip strength in the mice increased in the control group due to the exercise training: baseline 88.9±1.8 graphite force (gf) and day 28: 119.8±6.4 gf. Forelimb grip strength increased in the 1-methylxanthine group from baseline 91.1±1.3 gf, to day 28 126.9±6.0 gf. The changes in strength observed in 1-methylxanthine group were 15.9% greater than control.

2.1.2. Effect of Supplementation on Treadmill Performance

The distance travelled by mice during the treadmill exercise increased from 267.1±29.3 cm to 1,514.4±126.1 cm in the control group due to the exercise training. Distance travelled in the 1-methylxanthine group increased from baseline 269.6±33.0 cm, to day 28: 1,641.3±74.6. The changes in treadmill performance observed in 1-methylxanthine group were 10.0% greater than control.

2.1.3. Effect of Supplementation on Muscle Mass and Organ Weight

The gastrocnemius mass levels were 1.9% greater 28 days after 1-methylxanthine supplementation (161.1±4.3 mg) when compared to control (158.1±1.9 mg).

2.2. 1-Methylxanthine Plus Paraxanthine 2.2.1. Effect of Supplementation on Forelimb Grip Strength Forelimb grip strength in the mice increased in the 1-Methylxanthine plus paraxanthine group from baseline 91.2±0.9 graphite force (gf) and day 28: 130.7±7.9 gf. The changes in strength observed in 1-methylxanthine plus paraxanthine group were 27.8% greater than control, and 10.3% greater than 1-methylxanthine.

2.2.2. Effect of Supplementation on Treadmill Performance

Distance travelled in the 1-methylxanthine plus paraxanthine group increased from baseline 280.0±27.0 cm to day 28: 1,703.5±70.3. The changes in treadmill performance observed in 1-methylxanthine plus paraxanthine group were 14.1% greater than control, and 7.7% greater than 1-methylxanthine.

2.2.3. Effect of Supplementation on Muscle Mass and Organ Weight

The gastrocnemius mass levels were 3.3% greater 28 days after 1-methylxanthine plus paraxanthine supplementation (163.3±3.4 mg) when compared to control (158.1±1.9 mg), and 1.4% greater when compared 1-methylxanthine.

There was no difference in organ weight between treatment groups and control. Liver weight (mg) was control 1874.75±24.88; 1-MX 1847.25±47.92; paraxanthine+1-MX 1884.63±27.28. Heart weight (mg) was control 189.38±1.85; 1-MX 189.13±0.64; paraxanthine+1-MX 189.25±1.16

Example 2

Cognition, Memory, Learning 1.1. Methods

Behavioral studies were conducted in mice to examine the learning and memory ability by using Cook's pole and Passive shock avoidance test.

Twenty-four 8-week-old male Swiss Albino mice were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into three groups (n=8 per group in each test) for oral treatment once a day, at approximately same time each day (±1 hour), for 7 consecutive days: (1) vehicle control or (2) 1-methylxanthine or (3) 1-methylxanthine plus paraxanthine. The dose administered to the mice was calculated using US Food and Drug Administration for human equivalence doses (HED), assuming a human weight of 60 kg. The following HED was used in this study: 100 mg 1-methylxanthine (Ingenious Ingredients, L.P Lewisville, TX, USA; mouse dose: 20.5 mg/kg bw/day), or 100 mg 1-methylxanthine (Ingenious Ingredients, L.P Lewisville, TX, USA; mouse dose: 20.5 mg/kg bw/day) plus 100 mg paraxanthine (ENFINITY™, Ingenious Ingredients, L.P Lewisville, TX, USA; mouse dose: 20.5 mg/kg bw/day). 0.5% Carboxy Methyl Cellulose sodium was used as vehicle and the test item formulations were prepared daily. Dosing was conducted via oral gavage using disposable polypropylene syringes with sterilized stainless steel gavage tubes. Food intake was monitored daily while water intake was ad libitum.

1.2. Cook's Pole Climbing Test

Mice were trained in such a way that the animal had to climb the pole (shock free zone) within 30 seconds to avoid a shock. The shock was preceded by a buzzer that lasted for 15 seconds. The animals were trained to climb the pole at the sound of the buzzer (conditioned avoidance response). At particular intervals, 20 trials were given for each animal and average of the shock avoidance and mistakes were recorded. Trained animals were assayed by conditioned avoidance responses.

1.3. Passive Shock Avoidance Test

The apparatus consisted of a light and a dark compartment with a grid floor adjoining each other through a small gate. The animals were accustomed to the behavioral apparatus during two consecutive days (5 min in each day) before the training session. In the training phase, the mice were placed in the light compartment facing away from the dark compartment. When the animals were entered completely into the dark compartment, they received an electric shock (20V with AC current of 5 mA). The mice were then returned to their home cage. The animals were placed in the light compartment, and the time latency for entering the dark compartment as well as the time spent by the animals in the dark and light compartments was recorded and defined as the retention trial.

1.4. Induction of Amnesia

Amnesia was induced by using the scopolamine injection. Scopolamine is an anti-cholinergic and is an attractive amnesic agent for discerning the action of candidate anti amnesic drugs. Scopolamine is a non-selective post synaptic muscarinic receptor blocker and can cause cognitive impairments in rodents and humans via decreasing the effectiveness of ACH in the CNS in animals and humans. Scopolamine can induce the significant deficits in cognitive performance on behavioral tests which makes it a valid pharmacological model for inducing cognitive deficits. In this study to evaluate the cognitive effect, the mice were injected with scopolamine intraperitoneally to induce memory deficits.

2. Results

The mice treated with 1-methylxanthine showed reversal of amnesia induced by scopolamine and improved memory and learning. The combination of 1-methylxanthine and paraxanthine showed additional benefits over 1-methylxanthine alone.

2.1. 1-Methylxanthine 2.1.1. Effect of Supplementation on Cook's Pole Climbing Test Escape latency in 1-methylxanthine group (10.13±0.83 seconds) was 14.9% faster than control (11.88±0.64 seconds).

2.1.2. Effect of Supplementation on Passive Shock Avoidance Test

Transfer latency in 1-methylxanthine group (24.25±2.60 seconds) was 9.3% faster than control (26.75±2.60 seconds).

2.2. 1-Methylxanthine Plus Paraxanthine 2.1.1. Effect of Supplementation on Cook's Pole Climbing Test Escape latency in 1-methylxanthine plus paraxanthine group (8.75±1.98 seconds) was 26.3% faster than control (11.88±0.64 seconds), and 13.6% faster than the 1-methylxanthine group (10.13±0.83 seconds).

2.1.2. Effect of Supplementation on Passive Shock Avoidance Test

Transfer latency in 1-methylxanthine plus paraxanthine group (18.63±1.30 seconds) was 30.4% faster than control (26.75±2.60 seconds), and 22.3% faster than the 1-methylxanthine group (24.25±2.60 seconds).

Example 3

Energy, Mood, Endurance 1.1. Methods

Twenty-four 8-week-old male Swiss Albino mice were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into three groups (n=8 per group in each test) for oral treatment once a day, at approximately same time each day (±1 hour), for 28 consecutive days: (1) vehicle control or (2) 1-methylxanthine or (3) 1-methylxanthine plus paraxanthine. The dose administered to the mice was calculated using US Food and Drug Administration for human equivalence doses (HED), assuming a human weight of 60 kg. The following HED was used in this study: 100 mg 1-methylxanthine (Ingenious Ingredients, L.P Lewisville, TX, USA; mouse dose: 20.5 mg/kg bw/day), or 100 mg 1-methylxanthine (Ingenious Ingredients, L.P Lewisville, TX, USA; mouse dose: 20.5 mg/kg bw/day) plus 100 mg paraxanthine (ENFINITY™, Ingenious Ingredients, L.P Lewisville, TX, USA; mouse dose: 20.5 mg/kg bw/day). 0.5% Carboxy Methyl Cellulose sodium was used as vehicle and the test item formulations were prepared daily. Dosing was conducted via oral gavage using disposable polypropylene syringes with sterilized stainless steel gavage tubes. Food intake was monitored daily while water intake was ad libitum.

1.2. Forced Swim Test

During treatment period, training was accomplished on a swimming chamber at a moderate room temperature for 15 mins. The animals were adapted to this procedure daily 1 hr after dosing for 5 days in a week during the treatment period. On 28th day of respective treatment of all the animals were subjected to force swim test. Animals were forced to swim individually for 30 min in a glass jar of height 20 cm, diameter 10 cm, and filled with fresh water to a depth of 15 cm at room temperature. The parameters measured were first occurrence of climbing (the period the animal tries to climb the wall of the chamber), duration of immobility (the total time during which the animal is immobile) and total time spent in active swimming (the total duration during which the animal swims throughout the experimental period).

2. Results

The mice treated with 1-methylxanthine showed improved energy and endurance, improved mood. The combination of 1-methylxanthine and paraxanthine showed additional benefits over 1-methylxanthine alone.

2.1. 1-Methylxanthine

Duration of immobility was 5.4% lower in 1-methylxanthine group (9.74±0.79 minutes) compared to control (10.30±0.97 minutes).

The duration of mobility/active swimming was 2.8% greater in 1-methylxanthine group (20.26±0.79 minutes) compared to control (19.70±0.97 minutes).

The number of climbing improved by 6.0% in 1-methylxanthine group (6.7±1.16) compared to control (7.13±1.36).

2.2. 1-Methylxanthine Plus Paraxanthine

Duration of immobility was 12.6% lower in the 1-methylxanthine plus paraxanthine group (9.00±0.72 minutes) compared to control (10.30±0.97 minutes) and 7.6% lower compared to 1-methylxanthine group (9.74±0.79 minutes).

The duration of mobility/active swimming was 6.6% greater in the 1-methylxanthine plus paraxanthine group (21.00±0.72 minutes) compared to control (19.70±0.97 minutes), and 3.7% greater compared to the 1-methylxanthine group (20.26±0.79 minutes).

The number of climbing improved by 31.6% in 1-methylxanthine plus paraxanthine group (4.88±1.13) compared to control (7.13±1.36), and by 27.1%% compared the 1-methylxanthine (6.7±1.16).

There was no difference in organ weight between treatment groups and control. Liver weight (mg) was control 1865.38±48.57; 1-MX 1850.88±39.96; paraxanthine+1-MX 1864.38±44.68. Heart weight (mg) was control 190.38±1.85; 1-MX 188.50±3.12; Paraxanthine+1-MX 188.25±5.20.

Example 4

Cognition, Antioxidant, Neuroprotection, Alzheimer's (Young and Old)

1. Methods

Twenty-four young (6-8 Week) and twenty-four old (14-16 Months) Swiss Albino Wistar rats were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight and age into six groups (n=8 per group in each test) for oral treatment once a day, at approximately same time each day (±1 hour), for 10 consecutive days: (1) vehicle control or (2) 1-methylxanthine or (3) 1-methylxanthine plus paraxanthine. The dose administered to the rat was calculated using US Food and Drug Administration for human equivalence doses (HED), assuming a human weight of 60 kg. The following HED was used in this study: 100 mg 1-methylxanthine (Ingenious Ingredients, L.P Lewisville, TX, USA; rat dose: 10.283 mg/kg bw/day), or 100 mg 1-methylxanthine (Ingenious Ingredients, L.P Lewisville, TX, USA; rat dose: 10.283 mg/kg bw/day) plus 25 mg paraxanthine (ENFINITY™, Ingenious Ingredients, L.P Lewisville, TX, USA; rat dose: 2.57 mg/kg bw/day). 0.5% Carboxy Methyl Cellulose sodium was used as vehicle and the test item formulations were prepared daily. Dosing was conducted via oral gavage using disposable polypropylene syringes with sterilized stainless steel gavage tubes. Food intake was monitored daily while water intake was ad libitum. All the animals were subjected to Walter Morris Maze training 4 times at 4 starting points continued daily for 4 days. Body weight was recorded weekly. On the last day, blood was collected from retro-orbital route for biochemical analysis and animals were sacrificed using anesthesia. All the weighable organs (brain) were collected, weighed and preserved in Buffer for histopathology. Serum samples was separated to estimate various biochemical parameters.

Walter Morris Water Maze Test (MWMT): The Morris water maze consisted of a circular pool in a room with geometric shapes on the wall serving as spatial cues. The pool, which is 70 cm in diameter and painted with black color, filled with 13 cm depth of 25±1° C. water. A platform (6 cm diameter) was placed into one quadrant of the pool and submerged 1 cm below the water surface. For the training, all rats were trained to locate the submerged platform in constant location. The training day consisted of four trials. During training, a rat started at one of four starting points and allowed to swim until it located the platform or until 60 seconds had elapsed. The rat was allowed to remain on the platform for 15 seconds before being dried off and later was transferred to a holding cage. If the rat did not reach the platform within 60 seconds, it was gently guided there by the experimenter. The animals were continuously trained 4 times at 4 starting points continued daily for 4 days, the main trial was conducted on the 15th day and the latency of escaping onto the platform was recorded.

2. Results 2.1. 1-MX Increases Cognitive Performance in Young and Old Rats

Escape latency significantly increased in the 1-MX group compared to the control group in young rats (32.18±1.10 seconds for 1-MX vs. 53.02±1.92 seconds in the control group). Escape latency increased in old rats compared to young rats indicating age-related cognitive decline (56.88±1.79 seconds vs. 53.02±1.92 young rats), and supplementation of 1-MX in old rats reversed the age-related cognitive decline and improved cognitive performance (41.71±1.81 seconds in the 1-MX group compared to the control group, 56.88±1.79 seconds) and improved cognition in old rats over young rats.

2.2. 1-MX Increases Neurotransmitter Levels in Young and Old Rats

1-MX significantly increased neurotransmitter levels in young (acetylcholine: 63.35±4.12 U/ml for 1-MX vs 58.65±3.42 U/ml for control; and dopamine 582.33±17.02 ng/L for 1-MX and 474.30±27.41 ng/L for control). Aging decreased neurotransmitter levels (acetylcholine from 58.65±3.42 U/ml to 52.64±2.73 U/ml; dopamine from 474.30±27.41 ng/L to 404.54±23.41 ng/L). Supplementation with 1-MX reversed the negative effect of aging and significantly increased neurotransmitter levels (52.64±2.73 U/ml to 56.33±3.42 U/ml for acetylcholine and 404.54±23.41 ng/L to 474.42±13.49 ng/L for dopamine).

2.3. 1-MX Increases Brain Protection in Young and Old Rats

Brain-derived neurotrophic factor (BDNF) is a protein found in the brain and spinal cord that promotes the survival of nerve cells by playing a role in the growth, maturation, and maintenance of these cells.

1-MX supplementation significantly increased BDNF levels in young rats (from 775.04±29.59 pg/mL in the control group to 869.04±32.79 pg/mL in the 1-MX group. Aging reduced BDNF levels (from 775.04±29.59 pg/mL to 732.16±16.51 pg/mL) and supplementation of old rats with 1-MX significantly increased BDNF levels to 793.81±33.85 pg/mL, not only reversing the negative effects of aging, but increasing levels over those of young rats.

2.4. 1-MX Increases Antioxidant Levels in Young and Old Rats

1-MX supplementation significantly increased glutathione levels in young rats (from 21.85±1.35 μg/mL in the control group to 28.57±1.36 μg/mL in the 1-MX group. Aging reduced glutathione levels (from 21.85±1.35 μg/mL to 19.74±1.14 μg/mL) and supplementation of old rats with 1-MX significantly increased BDNF levels to 25.29±0.93 μg/mL, not only reversing the negative effects of aging, but increasing levels over those of young rats.

2.4. 1-MX Increases Antioxidant Levels in Young and Old Rats

1-MX supplementation significantly increased glutathione levels in young rats (from 21.85±1.35 μg/mL in the control group to 28.57±1.36 μg/mL in the 1-MX group. Aging reduced glutathione levels (from 21.85±1.35 μg/mL to 19.74±1.14 μg/mL) and supplementation of old rats with 1-MX significantly increased BDNF levels to 25.29±0.93 μg/mL, not only reversing the negative effects of aging, but increasing levels over those of young rats.

2.5. 1-MX Reduces Oxidative Stress in Young and Old Rats

1-MX supplementation significantly increased catalase levels in young rats (from 27.76±1.21 U/mL in the control group to 33.32±1.68 U/mL in the 1-MX group. Aging reduced catalase levels (from 27.76±1.21 U/mL to 26.16±1.03 U/mL) and supplementation of old rats with 1-MX significantly increased catalase levels to 32.78±1.26 U/mL, not only reversing the negative effects of aging, but increasing levels over those of young rats.

2.6. 1-MX Reduces Amyloid β-Protein (Aβ) 1-40 in Young and Old Rats

Deposition of amyloid β-protein (Aβ) as amyloid fibrils or nanofibrillar amorphous aggregates in senile plaques characterizes the Alzheimer disease (AD) brain. 1-MX supplementation significantly decreased Amyloid β-Protein (Aβ) 1-40 levels from 410.68±14.04 g/mL to 317.77±22.54 g/mL in aged rats, and from 295.09±12.39 g/mL to 254.60±7.43 g/mL in young rats.

2.7. Addition of PX to 1-MX Increases Cognitive Performance, Neurotransmitter Levels, Brain Protection, Antioxidant Levels and Reduced Amyloid Levels The co-administration of 25 mg HED paraxanthine (PX) with 100 mg HED 1-MX increased cognitive performance in young (53.02±1.92 seconds in the control group, 32.18±1.10 seconds in the 1-MX group, and 23.02±1.61 seconds in the 1-MX+PX group) and old rats (56.88±1.79 seconds in the control group, 41.71±1.81 seconds in the 1-MX group, and 33.30±1.92 seconds in the 1-MX+PX group).

The co-administration of 25 mg HED paraxanthine (PX) with 100 mg HED 1-MX increased neurotransmitter levels in young (acetylcholine from 58.65±3.42 U/ml in the control group to 63.35±4.12 U/ml in the 1-MX group and 66.80±3.06 U/ml in the 1-MX+PX group; dopamine from 474.30±27.41 ng/L in the control group to 530.58±37.50 ng/L in the 1-MX group and 584.40±17.87 ng/L in the 1-MX+PX group) and old rats (acetylcholine from 52.64±2.73 U/ml in the control group to 56.33±3.58 U/ml in the 1-MX group and 58.75±3.24 U/ml in the 1-MX+PX group; dopamine from 404.54±23.41 ng/L in the control group to 474.42±13.49 ng/L in the 1-MX group and 516.88±33.27 ng/L in the 1-MX+PX group).

The co-administration of 25 mg HED paraxanthine (PX) with 100 mg HED 1-MX increased Brain-derived neurotrophic factor (BDNF) levels in young (775.04±29.59 pg/mL in the control group to 869.04±32.79 pg/mL in the 1-MX group and 909.91±17.77 pg/mL in the 1-MX+PX group) and old rats (732.16±16.51 pg/mL in the control group to 793.81±33.85 pg/mL in the 1-MX group and 838.19±24.89 pg/mL in the 1-MX+PX group).

The co-administration of 25 mg HED paraxanthine (PX) with 100 mg HED 1-MX increased glutathione levels in young (21.85±1.35 μg/mL in the control group to 28.57±1.65 μg/mL in the 1-MX group and 33.43±1.80 μg/mL in the 1-MX+PX group) and old rats (19.74±1.14 μg/mL in the control group to 25.29±0.93 μg/mL in the 1-MX group and 27.34±1.11 μg/mL in the 1-MX+PX group).

The co-administration of 25 mg HED paraxanthine (PX) with 100 mg HED 1-MX increased catalase levels in young (27.76±1.21 U/mL in the control group to 33.32±1.68 U/mL in the 1-MX group and 37.86±1.42 U/mL in the 1-MX+PX group) and old rats (26.16±1.03 U/mL in the control group to 32.78±1.26 U/mL in the 1-MX group and 35.93±1.07 U/mL in the 1-MX+PX group).

The co-administration of 25 mg HED paraxanthine (PX) with 100 mg HED 1-MX decreased Amyloid β-Protein (Aβ) 1-40 levels from 295.09±12.39 g/mL in the control group to 254.60±7.43 g/mL in the 1-MX group to 222.44±12.62 g/mL in the 1-MX+PX group in aged rats.

There was no difference in brain weight between the treatment groups and control in either young or aged groups. Brain weight (mg) was: control young animals 1.724±0.034; 1-MX young animals 1.729±0.027; Paraxanthine+1-MX young animals 1.714±0.046; control aged animals 1.965±0.048; 1-MX aged animals 1.995±0.074; paraxanthine+1-MX aged animals 1.968±0.037.

Example 5

Safety/Toxicity

An acute oral toxicity study of 1-Methylxanthine) was conducted in female wistar rats in accordance with OECD 423 guidelines. Rats were administered a single dose of 2,000 mg/kg orally and then observed individually for the first four hours, then over a period of 24 hours and once daily for 14 days. General behavior, adverse effects and mortality were observed throughout the experimental period. Body weights were recorded on test day 0 (prior to administration), day 3, day 7 and day 14. All the animals were necropsied and examined macroscopically. All the surviving animals had gained body weight by day 14 as compared to day 0. No abnormalities were detected for the animals necropsied at terminal sacrifice. The limit doses of 2,000 mg/kg did not cause any mortality or signs of toxicity in the rats tested during the observation period. Based on the results, the median lethal dose of test substance in female rats after single oral treatment is 2,000 mg/kg body weight and is classified as category 5 and safe.

1-MX is significantly safer compared to caffeine. The oral median lethal dose of caffeine in albino rats was estimated to be (±S.E.) 0.192±0.018 g per kilogram body weight. The clinical signs of poisoning from these doses were schizophreniform withdrawal, hyperreflexia, vertigo, ataxia, evidence of pain, cataleptic stances, cataplexy, diarrhea, anuria, anorexia, adipsia, hypothermia, blepharitis, and loss of body weight. Death occurred in (±S.D.) 30±9.6 hours and was immediately due to respiratory failure following tetanic convulsions or to cardiovascular collapse. Autopsy revealed the presence of a fulminating gastroenteritis, congestion of the lungs, hepatitis, nephritis, toxic effects upon the heart, spleen, pancreas, thymus gland, adrenal glands, and dehydration of many organs and tissues. Survival was characterized by a marked polydipsia and polyuria (Reference: E. M. Boyd: The acute oral toxicity of caffeine, Toxicology and Applied Pharmacology 1959, 1 (3):250-257, https://doi.org/10.1016/0041-008X(59)90109-7).

1-MX is significantly safer compared to 3-methylxanthine (3-MX). The effects of 3-MX, the pharmacologically active metabolite of theophylline, on the kidneys of Wistar rats after short-term administration were studied. 3-MX was administered in oral doses of 0 (control), 50, 100 and 200 mg per kg per day for 1, 8 and 16 days. The kidneys were examined by light and electron microscopy. Tubular necrosis was noticed at a dose level of 100 mg kg$^{-1}$ after 16 days and at a dose level of 200 mg kg$^{-1}$ after 8 days. Elevated values of serum urea were found after 1 day of treatment with a dose of 200 mg kg$^{-1}$ and after 16 days with a dose of 100 mg kg$^{-1}$. Elevated values of serum creatinine were detected after 8 days of treatment with a dose of 200 mg kg$^{-1}$. The results indicate dose- and time-related renal failure following administration of 3-MX (Reference: P. Sellman, P. J. Klemi: Kidney toxicity of 3-methylxanthine in the rat. J Appl Toxicol 1984, 4(6):304-7. doi: 10.1002/jat.2550040605).

Example 6

Fat Burning: Respiratory Quotient
1. Methods

Upon determination of baseline respiratory quotient ($RQ=VCO_2/VO_2$) two participants were assigned in a randomized, double-blind, placebo-controlled, crossover fashion to ingest a non-energetic placebo (maltodextrin) or a 200 mg dose of 1-methylxanthine (1-MX), or a 200 mg dose of caffeine (CA). All supplements were orally ingested with 8 fluid ounces of cold tap water. The order of administration for all interventions was randomized using a random allocation software to ensure randomization and to avoid order effects. After ingestion, participants completed all assessments in an identical fashion 30, 60, 90, 120, and 180 minutes after ingestion of their assigned supplement. All study visits took place between 0600-1000 hours. At least 72 hours of rest will take place between each condition.
2. Results

TABLE 2

Subject's Characteristics

| Gender | Male | Female |
|---|---|---|
| Age (years) | 23 | 24 |
| Height (cm) | 175 | 168 |
| Body Mass Index (kg/m2) | 28.5 | 24.1 |
| Fat Mass (kg) | 18.8 | 14 |
| Fat-Free Mass (kg) | 67.4 | 14.6 |
| % Fat | 21.8 | 20.6 |
| Screening Body Mass (kg) | 87.2 | 68.1 |
| Screening Heart Rate (beats/min) | 56 | 61 |
| Screening Systolic Blood Pressure (mm Hg) | 117 | 109 |
| Screening Diastolic Blood Pressure (mm Hg) | 76 | 64 |

The lower the RQ, the more fat that is being oxidized for body energy needs. The closer to 1.0 the more carbohydrate is being burned for energy needs. If numbers are lower more fat is being oxidized.

1-MX reduced the respiratory quotient compared to placebo by 15%, resulting in greater fat loss. In addition, 1-MX showed greater fat loss than CA, by 2.3%.

TABLE 3

| | Condition | Time | Male, age 23 | Female, age 24 | Average |
|---|---|---|---|---|---|
| Respiratory Quotient | Placebo | 0 | 0.77 | 0.70 | |
| | | 30 | 0.72 | 0.92 | |
| | | 60 | 0.85 | 0.72 | |
| | | 90 | 0.94 | 0.76 | |
| | | 120 | 0.80 | 0.88 | |
| | | 180 | 0.81 | 0.69 | |
| | MEAN (30-180) | | 0.824 | 0.794 | 0.809 |
| | 200 mg 1-MX | 0 | 0.67 | 0.70 | |
| | | 30 | 0.69 | 0.72 | |
| | | 60 | 0.66 | 0.71 | |
| | | 90 | 0.67 | 0.66 | |
| | | 120 | 0.69 | 0.68 | |
| | | 180 | 0.67 | 0.70 | |

TABLE 3-continued

| Condition | Time | Male, age 23 | Female, age 24 | Average |
|---|---|---|---|---|
| MEAN (30-180) | | 0.676 | 0.694 | 0.685 |
| Δ vs. PLA | | −0.148 (−18%) | −0.10 (−13%) | −0.124 (−15%) |
| 200 mg Caffeine | 0 | 0.68 | 0.76 | |
| | 30 | 0.70 | 0.70 | |
| | 60 | 0.65 | 0.71 | |
| | 90 | 0.70 | 0.71 | |
| | 120 | 0.74 | 0.71 | |
| | 180 | 0.73 | 0.66 | |
| MEAN (30-180) | | 0.704 | 0.698 | 0.701 |
| Δ vs. PLA | | −0.120 (−15%) | −0.096 (−12%) | −0.108 (−13%) |
| Δ vs. 1-MX | | +0.028 (+4%) | +0.004 (+1%) | +0.016 (+2.3%) |

Example 7

Resting Energy Expenditure

1. Methods

Two participants were assigned in a randomized, double-blind, placebo-controlled, crossover fashion to ingest a non-energetic placebo (maltodextrin) or a 200 mg dose of 1-methylxanthine (1-MX). All supplements were orally ingested with 8 fluid ounces of cold tap water. Resting Energy Expenditure was measured at baseline, 30, 60, 90, 120 and 180 minutes after ingestion.

2. Results

1-MX increased kcal per day by 103 compared to placebo. Increased energy expenditure will result in weight loss.

TABLE 4

Resting Energy Expenditure

| | Condition | Time | Male, age 23 | Female, age 24 | Average |
|---|---|---|---|---|---|
| Resting Energy Expenditure (kcals/day) | Placebo | 0 | 2,076 | 1,911 | 1,994 |
| | | 30 | 2,034 | 1,450 | |
| | | 60 | 1,919 | 1,829 | |
| | | 90 | 1,723 | 1,765 | |
| | | 120 | 2,153 | 1,485 | |
| | | 180 | 1,905 | 1,674 | |
| | MEAN | | 1,947 | 1,641 | 1,794 |
| | Mean Δ from 0 | | −129 | −270 | −200 |
| | 200 mg 1-MX | 0 | 2017 | 1769 | |
| | | 30 | 2050 | 1789 | |
| | | 60 | 1975 | 1790 | |
| | | 90 | 1988 | 1777 | |
| | | 120 | 1964 | 1912 | |
| | | 180 | 2053 | 1670 | |
| | MEAN | | 2,006 | 1,788 | 1,897 |
| | Δ vs. PLA | | +59 (+3.0%) | +147 (+9.0%) | +103 (+5.7%) |

Example 8

Heart Rate, Blood Pressure

1. Methods

Two participants were assigned in a randomized, double-blind, placebo-controlled, crossover fashion to ingest 200 mg dose of 1-methylxanthine (1-MX) or 200 mg of caffeine (CA). All supplements were orally ingested with 8 fluid ounces of cold tap water. Resting Heart Rate, Systolic and Diastolic Blood Pressure was measured at baseline, 30, 60, 90, 120 and 180 minutes after ingestion.

2. Results

CA ingestion increased mean heart rate from baseline by 10%, diastolic by 20.3% and systolic blood pressure by 17.2%. In comparison to CA, 1-MX reduced heart rate by 3%, diastolic by 12%, and systolic blood pressure by 6.1%. 1-MX did not increase heart rate or systolic blood pressure from baseline.

TABLE 5

Resting Heart Rate

| | Condition | Time | Male, age 23 | Female, age 24 | Average |
|---|---|---|---|---|---|
| Resting Heart Rate (bpm) | 200 mg Caffeine | 0 | 49 | 59 | |
| | | 30 | 64 | 65 | |
| | | 60 | 56 | 62 | |

TABLE 5-continued

| | Resting Heart Rate | | | | |
|---|---|---|---|---|---|
| | Condition | Time | Male, age 23 | Female, age 24 | Average |
| | | 90 | 51 | 62 | |
| | | 120 | 61 | 64 | |
| | | 180 | 44 | 69 | |
| | MEAN (30-180) | | 55.2 | 63.6 | 59.4 |
| | Mean Δ from 0 | | +6.2 | +4.6 | +5.4 (+10%) |
| | 200 mg 1-MX | 0 | 65 | 65 | |
| | | 30 | 63 | 61 | |
| | | 60 | 54 | 60 | |
| | | 90 | 49 | 65 | |
| | | 120 | 45 | 60 | |
| | | 180 | 55 | 62 | |
| | MEAN (30-180) | | 53.2 | 62.6 | 57.9 (−3%) |
| | Δ vs. CA | | −2.0 | −1.0 | −1.5 (−3%) |
| | Mean Δ from 0 | | −11.8 | −2.4 | −9.6 |

TABLE 6

| | Systolic Blood Pressure | | | | |
|---|---|---|---|---|---|
| | Condition | Time | Male, age 23 | Female, age 24 | Average |
| Systolic Blood Pressure (mm Hg) | 200 mg Caffeine | 0 | 105 | 108 | |
| | | 30 | 137 | 124 | |
| | | 60 | 131 | 122 | |
| | | 90 | 132 | 125 | |
| | | 120 | 123 | 114 | |
| | | 180 | 127 | 113 | |
| | MEAN (30-180) | | 130.0 | 119.6 | 124.8 |
| | Mean Δ from 0 | | +25.0 | +11.6 | +18.3 (+17.2%) |
| | 200 mg 1-MX | 0 | 125 | 113 | |
| | | 30 | 116 | 125 | |
| | | 60 | 136 | 110 | |
| | | 90 | 108 | 113 | |
| | | 120 | 116 | 114 | |
| | | 180 | 142 | 92 | |
| | MEAN (30-180) | | 123.6 | 110.8 | 117.2 |
| | Δ vs. CA | | −6.4 | −9.6 | −7.6 (−6.1%) |
| | Mean Δ from 0 | | −1.6 | −2.2 | −1.9 (−1.6%) |

TABLE 7

| | Diastolic Blood Pressure | | | | |
|---|---|---|---|---|---|
| | Condition | Time | Male, age 23 | Female, age 24 | Average |
| Diastolic Blood Pressure (mm Hg) | 200 mg Caffeine | 0 | 60 | 73 | |
| | | 30 | 77 | 77 | |
| | | 60 | 80 | 96 | |
| | | 90 | 83 | 84 | |
| | | 120 | 77 | 75 | |
| | | 180 | 76 | 77 | |
| | MEAN (30-180) | | 78.6 | 81.8 | 80.2 |
| | Mean Δ from 0 | | +18.6 | +8.8 | +13.7 (+20.3%) |
| | 200 mg 1-MX | 0 | 72 | 72 | |
| | | 30 | 71 | 79 | |
| | | 60 | 68 | 62 | |
| | | 90 | 69 | 70 | |
| | | 120 | 71 | 72 | |
| | | 180 | 79 | 65 | |
| | MEAN (30-180) | | 71.6 | 69.6 | 70.6 |
| | Δ vs. CA | | −5.0 | −12.2 | −9.6 (−12.0%) |
| | Mean Δ from 0 | | −0.4 | −2.4 | −1.4 |

Example 9

Anxiety
1. Methods

Two participants were assigned in a randomized, double-blind, placebo-controlled, crossover fashion to ingest 200 mg dose of 1-methylxanthine (1-MX) or 200 mg of caffeine (CA). All supplements were orally ingested with 8 fluid ounces of cold tap water. Anxiety was measured by Visual Analog Scale (VAS) at baseline, 30, 60, 90, 120 and 180 minutes after ingestion.

2. Results

CA ingestion increased perceived feelings of anxiety from baseline by 65%. In comparison to CA, 1-MX ingestion resulted in 21% lower feelings of anxiety. 1-MX did not increase heart rate or systolic blood pressure from baseline.

TABLE 8

Anxiety

| | Condition | Time | Male, age 23 | Female, age 24 | Average |
|---|---|---|---|---|---|
| Anxiety (Visual Analog Scale) | 200 mg Caffeine | 0 | 30 | 60 | |
| | | 30 | 61 | 70 | |
| | | 60 | 80 | 75 | |
| | | 90 | 80 | 76 | |
| | | 120 | 71 | 75 | |
| | | 180 | 81 | 75 | |
| | MEAN (30-180) | | 74.6 | 74.2 | 74.4 |
| | Mean Δ from 0 | | +44.6 | +14.2 | +29.3 (+65%) |
| | 200 mg 1-MX | 0 | 50 | 65 | |
| | | 30 | 51 | 65 | |
| | | 60 | 40 | 65 | |
| | | 90 | 40 | 65 | |
| | | 120 | 51 | 75 | |
| | | 180 | 61 | 75 | |
| | MEAN (30-180) | | 48.6 | 69.0 | 58.8 |
| | Δ vs. CA | | −26.0 | −5.2 | −15.6 (−21.0%) |
| | Mean Δ from 0 | | −1.4 | +4.0 | +1.3 |

Example 10

Concentration
1. Methods

One participant ingested 200 mg dose of 1-methylxanthine (1-MX) orally with 8 fluid ounces of cold tap water. Concentration was measured by Visual Analog Scale (VAS) at baseline, 30, 60, 90, 120 and 180 minutes after ingestion.

2. Results

1-MX ingestion increased perceived feelings of concentration from baseline by 6.4%.

TABLE 9

| | Condition | Time | Male, age 23 | Female, age 24 | Average |
|---|---|---|---|---|---|
| Concentration (Visual Analog Scale) | 200 mg 1-MX | 0 | 50 | 65 | |
| | | 30 | 60 | 65 | |
| | | 60 | 61 | 65 | |
| | | 90 | 50 | 65 | |
| | | 120 | 50 | 75 | |
| | | 180 | 51 | 70 | |
| | MEAN (30-180) | | 54.4 | 68.0 | 61.2 |
| | Mean Δ from 0 | | +4.4 (+8.8%) | +3.0 (+4.6%) | +3.7 (+6.4%) |

Example 11

Wakefulness
1. Methods

One participant ingested a non-energetic placebo (maltodextrin) followed by 200 mg dose of 1-methylxanthine (1-MX) one week later, orally with 8 fluid ounces of cold tap water. Wakefulness was measured by Visual Analog Scale (VAS) at baseline, 30, 60, 90, 120 and 180 minutes after ingestion.

2. Results

1-MX ingestion increased wakefulness from baseline by 15.0%, and by 12.0% over the placebo group.

TABLE 10

|  | Condition | Time | Female, age 24 |
|---|---|---|---|
| Wakefulness (Visual Analog Scale) | Placebo | 0 | 60 |
|  |  | 30 | 61 |
|  |  | 60 | 61 |
|  |  | 90 | 60 |
|  |  | 120 | 61 |
|  |  | 180 | 65 |
|  | MEAN |  | 61.6 |
|  | Mean Δ from 0 |  | +1.6 |
|  | 1-MX | 0 | 60 |
|  |  | 30 | 65 |
|  |  | 60 | 65 |
|  |  | 90 | 65 |
|  |  | 120 | 75 |
|  |  | 180 | 75 |
|  | MEAN |  | 69.0 |
|  | Δ vs. PLA |  | +7.4 (+12.0%) |
|  | Mean Δ from 0 |  | +9.0 (+15.0%) |

Example 12

Subject was a healthy adult male. Subject was administered 200 mg of 1-methylxanthine prior to work out. Subject reported increased focus, concentration, mood and performance during the work out.

During another trial subject was administered 100 mg of 1-methylxanthine together with 100 mg of paraxanthine, prior to work out. Subject reported a synergistic increase from the combination in focus, concentration, mood and performance during work out.

What is claimed is:

1. A method for increasing energy in a subject comprising administering to the subject a composition comprising an effective amount of 1-methylxanthine, wherein the amount of 1-methylxanthine administered is from about 50 mg to about 400 mg.

2. The method of claim 1, wherein the subject experiences an increase in perception of energy of at least about 5%.

3. The method of claim 1, wherein the subject experiences a decrease of at least one of anxiety, fatigue, perception of effort, and/or perception of pain.

4. The method of claim 1, wherein the composition further comprises paraxanthine in an amount from about 2 mg to about 800 mg.

5. The method of claim 4, wherein the administration of paraxanthine and 1-methylxanthine produces a synergistic increase in perception of energy in the subject, relative to the administration of a comparable dose of paraxanthine or 1-methylxanthine alone.

6. The method of claim 1, wherein the composition further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, *Magnolia* bark, theanine, phosphatidylserine, ashwagandha, *Rhodiola*, taurine, tyrosine, n-acetyl-tyrosine, macuna, *Sceletium tortuosa*, 5-HTP, tryptophan, saffron, Vitamin D, SAMe, lions mane and huperzine A.

7. The method of claim 1, wherein the composition is substantially free of caffeine.

8. A method for improving athletic performance in a subject in comprising administering to the subject a composition comprising an effective amount of 1-methylxanthine wherein the amount of 1-methylxanthine administered is from about 50 mg to about 400 mg and wherein the amount of paraxanthine is administered is from about 2 mg to about 800 mg.

9. The method of claim 8, wherein athletic performance is increased by at least about 10%.

10. The method of claim 8, wherein the subject experiences an increase in endurance.

11. The method of claim 8, wherein the composition further comprises paraxanthine in an amount from about 50 mg to about 400 mg and wherein administration of the composition to a subject produces a synergistic increase in athletic performance, relative to the administration of a comparable dose of paraxanthine or 1-methylxanthine alone.

12. The method of claim 8, wherein the composition further comprises at least one agent selected from the group consisting of L-theanine, phosphatidylcholine, alpha-GPC (L-alpha glycerylphosphorylcholine), Citicoline (Cytidine diphosphate choline (CPD Choline)), Choline Bitartrate, *Bacopa monnieri*, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, huperzine A, theacrine, methylliberine, B12, sulbutiamine, *Magnolia* bark, ketones, MCTs, omega 3's, lutein, zeaxanthin, tyrosine and n-acetyl-tyrosine, taurine, acetyl-1-carnitine and/or combinations thereof.

13. A method for increasing energy in a subject comprising administering to the subject a composition comprising an effective amount of 1-methylxanthine and paraxanthine, wherein the amount of 1-methylxanthine administered is from about 50 mg to about 400 mg and wherein the amount of paraxanthine is administered is from about 50 mg to about 400 mg wherein the administration of paraxanthine and 1-methylxanthine produce a synergistic increase in perception of energy in the subject, relative to the administration of a comparable dose of paraxanthine or 1-methylxanthine alone.

\* \* \* \* \*